(12) United States Patent
Hill et al.

(10) Patent No.: US 8,692,053 B2
(45) Date of Patent: *Apr. 8, 2014

(54) SOYBEAN GENE FOR RESISTANCE TO ALPHIS GLYCINES

(75) Inventors: Curtis B. Hill, Champaign, IL (US); Glen L. Hartman, Urbana, IL (US)

(73) Assignees: The Board of Trustees of the University of Illinois, Urbana, IL (US); The United States of America, as represented by the Secretary of Agriculture, Washington, DC (US)

( * ) Notice: Subject to any disclaimer, the term of this patent is extended or adjusted under 35 U.S.C. 154(b) by 423 days.

This patent is subject to a terminal disclaimer.

(21) Appl. No.: 13/005,372

(22) Filed: Jan. 12, 2011

(65) Prior Publication Data
US 2011/0154527 A1 Jun. 23, 2011

Related U.S. Application Data

(62) Division of application No. 11/869,500, filed on Oct. 9, 2007, now Pat. No. 7,928,286.

(60) Provisional application No. 60/829,123, filed on Oct. 11, 2006.

(51) Int. Cl.
*A01H 1/00* (2006.01)
*A01H 1/02* (2006.01)
*A01H 5/00* (2006.01)

(52) U.S. Cl.
USPC ........... 800/266; 800/265; 800/298; 800/312; 800/302; 435/415; 435/6.11

(58) Field of Classification Search
None
See application file for complete search history.

(56) References Cited

U.S. PATENT DOCUMENTS

| | | | | |
|---|---|---|---|---|
| 7,928,286 | B2 * | 4/2011 | Hill et al. ...................... | 800/266 |
| 2004/0261144 | A1 | 12/2004 | Martin et al. | |
| 2006/0014964 | A1 | 1/2006 | Duncia et al. | |
| 2006/0015964 | A1 | 1/2006 | Hill et al. | |
| 2009/0241214 | A1 | 9/2009 | Wang et al. | |

OTHER PUBLICATIONS

Hill, C.B., et al. (2005) "Resistance to the soybean aphid in soybean germplasm and other legumes," p. 179, World Soybean Research Conference, Foz do Iguassu, PR, Brazil.
Luginbill, J.P., "Developing resistent plants—The ideal method of controlling insects," (1969).
Patterson, J. and Ragsdale, D., "Assessing and managing risk from soybean aphids in the North Central States," (Apr. 11, 2002).
Sama, S. et al., "Varietal screening for resistance to the aphid, *Aphis glycines*, in soybean," (1974) *Research Reports 1968-1974*, pp. 171-172.

Wang et al. (1996) "Study on the effects of the population dynamics of soybean aphid (*Aphid glycines*) on both growth and yield of soybean," *Soybean Sci.* 15:243-247 (Abstract only).
Narvel et al (2001) "A Retrospective DNA Marker Assessment of the Development of Insect Resistant Soybean," *Crop. Sci.*, vol. 17, No. 5, pp. 1931-1939.
Auclair, J.L. (1989) "Host plant resistance," In; *Aphids: Their biology, natural enemies, and control*, vol. C. P. Harrewijn ed., Elsevier, New York, pp. 225-265.
Clark et al. (2002) "Transmissibility of Field Isolates of Soybean Viruses by *Aphis glycines*," *Plant Dis.* 86:1219-1222.
Cregan, P.B., et al., "An Integrated Genetic Linkage Map of the Soybean Genome" (1999) *Crop Sci.* 39:1464-1490.
Du Toit, F. (1987), "Resistance in wheat (*Triticum aestivum*) to *Diuraphis noxia* (Homoptera: Aphididae)," *Cereal Res. Commun.* 15:175-179.
Harrewijn, P. and Minks, A.K., "Integrated aphid management: General aspects," pp. 267-272, In A.K. Minks and P Harrewijn (ed.) *Aphids: Their biology, natural enemies, and control.* vol. C., Elsevier, New York (1989).
Hartman, G.L. et al., "Occurrence and distribution of *Aphis glycines* on soybeans in Illinois in 2000 and its potential control," (Feb. 1, 2001 availabe at the "plantmanagementnetwork" org website).
Hill, J.H. et al., "First report of transmission of *Soybean mosaic virus* and *Alfalfa Mosaic virus* by *Aphis glycines* in the New World," (2001) *Plant Dis.* 561.
Hill, C.B., et al. (2006), "A single dominant gene for resistance to the soybean aphid in the soybean cultivar Dowling," *Crop Sci.* 46:1601-1605.
Hill, C.B., et al. (2006), "Soybean aphid resistance in soybean Jackson is controlled by a single dominant gene," Crop Science 46:1606-1608.
Hill, C.B., et al. (2004), "Resistance of *Glycine* species and various cultivated legumes to the soybean aphid (Homoptera : Aphididae)," *J. Econ. Entomol.* 97:1071-1077.
Hill, C.B., et al. (2004), "Resistance to the soybean aphid in soybean germplasm," *Crop Sci.* 44:98-106.
Hymowitz, T., "On the domestication of the soybean," (1970) *Econ. Bot.* 24:408-421.
Iwaki, M. et al., "A persistent aphid borne virus of soybean, Indonesian *Soybean dwarf virus* transmitted by *Aphis glycines*," (1980) *Plant Dis.* 64:1027-1030.
Jeong, S.C. et al., "Cloning and Characterization of an Rga Family From The Soybean Molecular Linkage Group F," in an Abstract published by Plant & Animal Genome VIII Conference, Town & Country Hotel, San Diego, CA, Jan. 9-12, 2000 at a website address with the usual www prefix followed by intl-pag.org/8/abstracts/pag8255.html.

(Continued)

*Primary Examiner* — Medina A Ibrahim
(74) *Attorney, Agent, or Firm* — Ellen P. Winner; e winner & associates, pllc

(57) ABSTRACT

An *Aphis glycines* resistance Rag2 gene is provided herein, along with methods for identifying its presence using marker-assisted selection. A cultivar of *G. max* having resistance to *Aphis glycines* conferred by the Rag2 gene has been identified. The Rag2 gene, as well as the methods, aphid-resistant varieties, and markers disclosed herein may be used to breed new elite lines expressing soybean aphid resistance.

8 Claims, 14 Drawing Sheets

(56) References Cited

OTHER PUBLICATIONS

Jeong, S.C. and Saghai Maroof, M.A. (2004), "Detection and genotyping of SNPs tightly linked to two disease resistance loci, Rsv1 and Rsv3, of soybean," *Plant Breeding* 123:305-310.

Kaloshian, I., et al. (1997), "The impace of Meu-1-mediated resistance in tomato on lengevity, fecundity and behavior of the potato aphid," *Macrosiphum euphorbiae, Entomol. Exp. Appl.* 83:181-187.

Klinger, J. et al. (2001), "Mapping of cotton-melon aphid resistance in melon," *J. Am. Soc. Hortic. Sci.* 136:56-63.

Li, Y., et al., "Soybean aphid resistance genes in the soybean cultivars Dowling and Jackson map to linkage group M," *Mol. Breed.* 19(1):25-39.

Li, Y., et al. (2004) "Effect of three resistant soybean genotypes on the fecundity mortality, and maturation of soybean aphid (Homoptera : Aphididae)," *J. Econ. Entomol.* 97:1106-1111.

Ostlie, K., "Managing soybean aphid," Oct. 2, 2002.

Sun, Z. et al., "Study on the uses of aphid-resistant character in wild soybean. I. Aphid-resistance performance of $F_2$ generation from crosses between cultivated and wild soybeans," (1990) *Soybean Genet. News.* 17:43-48.

Tamulonis et al. (1997) "DNA marker analysis of loci conferring resistance to peanut root-knot nematode in soybean," *Theor. Appl. Genet.* 95:664-670.

Tyler et al. (1985) "Biotype E greenbug resistance in wheat streak mosaic virus-resistant wheat germplasm lines," *Crop Sci.* 25:686-688.

Wang et al. (2003), "A low-cost, high-throughput polyacrylamide gel electrophoresis system for genotyping with micro satellite DNA markers," *Crop Sci.* 43:1828-1832.

Wu, et al. (Feb. 2004) "A BAC and BIBAC-based physical map of the soybean genome" *Genome Res.* 14(2):319-26.

Yong et al. (1996), "Isolation of a superfamily of candidate disease-resistance genes in soybean based on a conserved nucleotide-binding side," *Proc. Nat. Acad. Sci. USA* 93:11751-11756.

Zhuang et al. (1996) "A Study on resistance to soybean mosaic virus and *Aphis glycines* of perennial wild soybean," *Soybean Genet. Newsl.* 23:66-69.

Jun T, et al. (2012), Theor Appl Genet 124:13-22.

Kang S, et al. (2008), Crop Sci 48:1744-1748.

Mensah C, et al. (2008), Crop Sci 48:1759-1763.

Mian et al. (2008), Crop Sci 48:1055-1061.

Mian et al. (2008), Theor Appl Genet 117:955-962.

Kim et al, (2010),Theor. Appl. Genet. 121:599-610.

Hill, et al. (2009), Crop Science 49:1193-1200.

\* cited by examiner

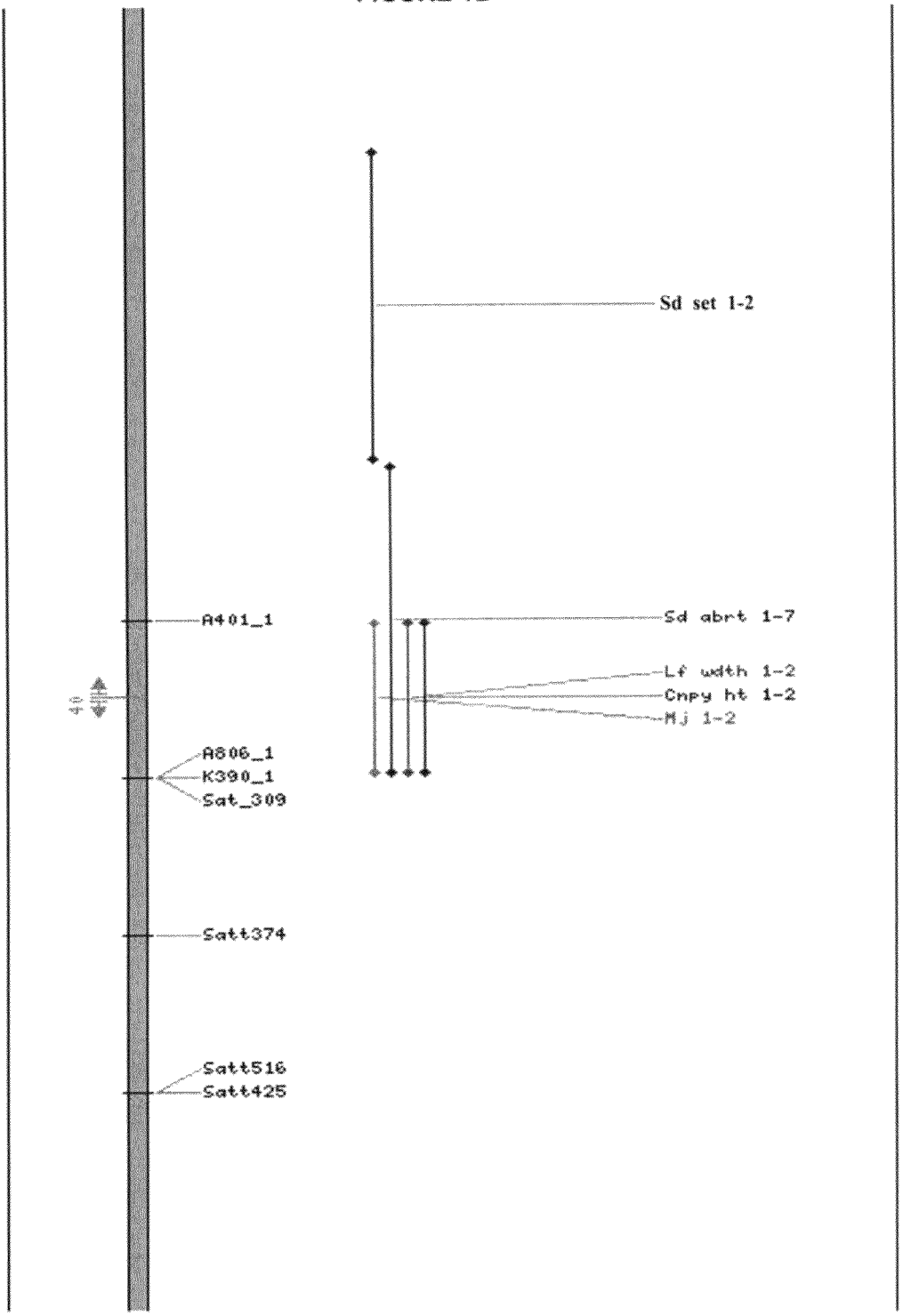

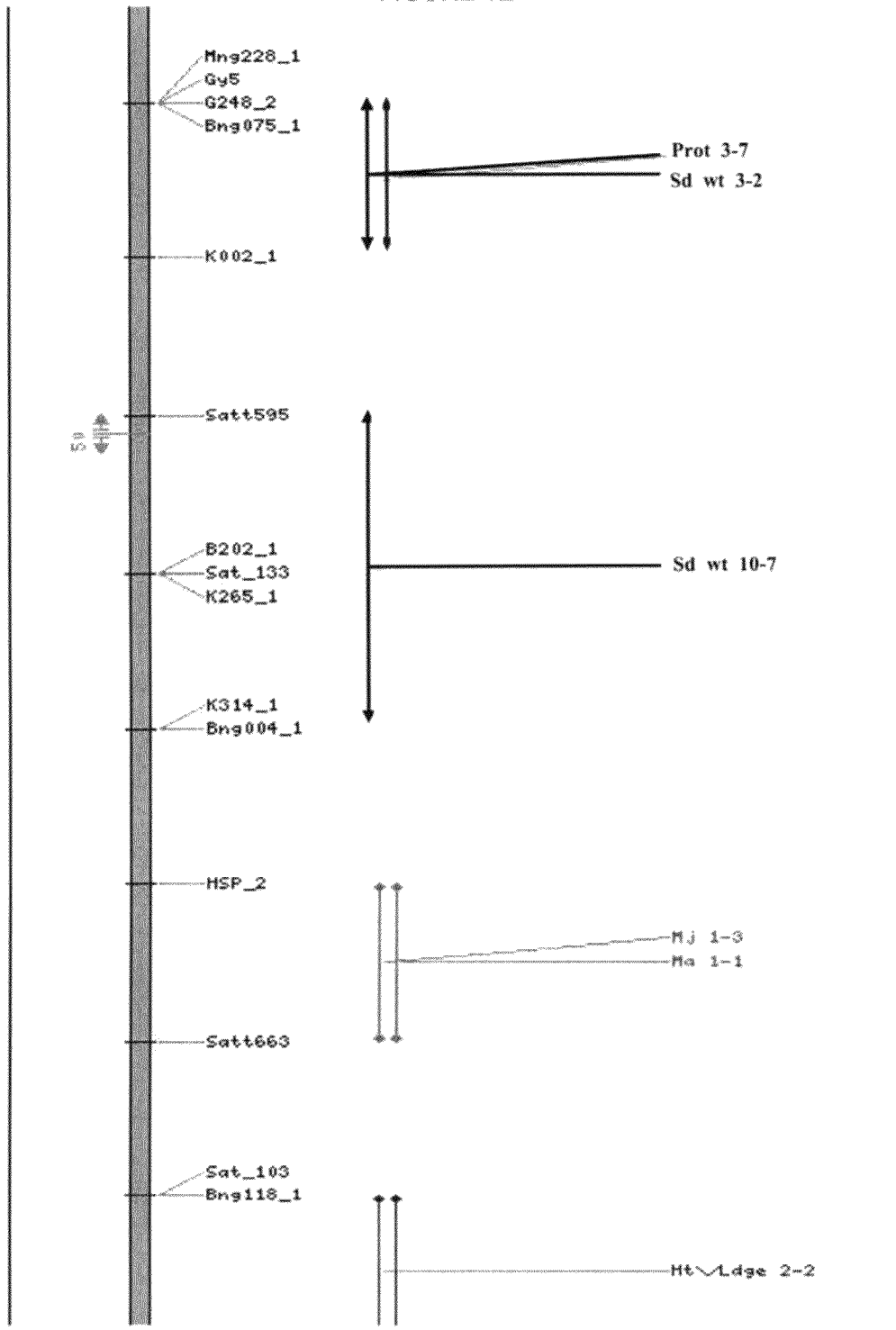

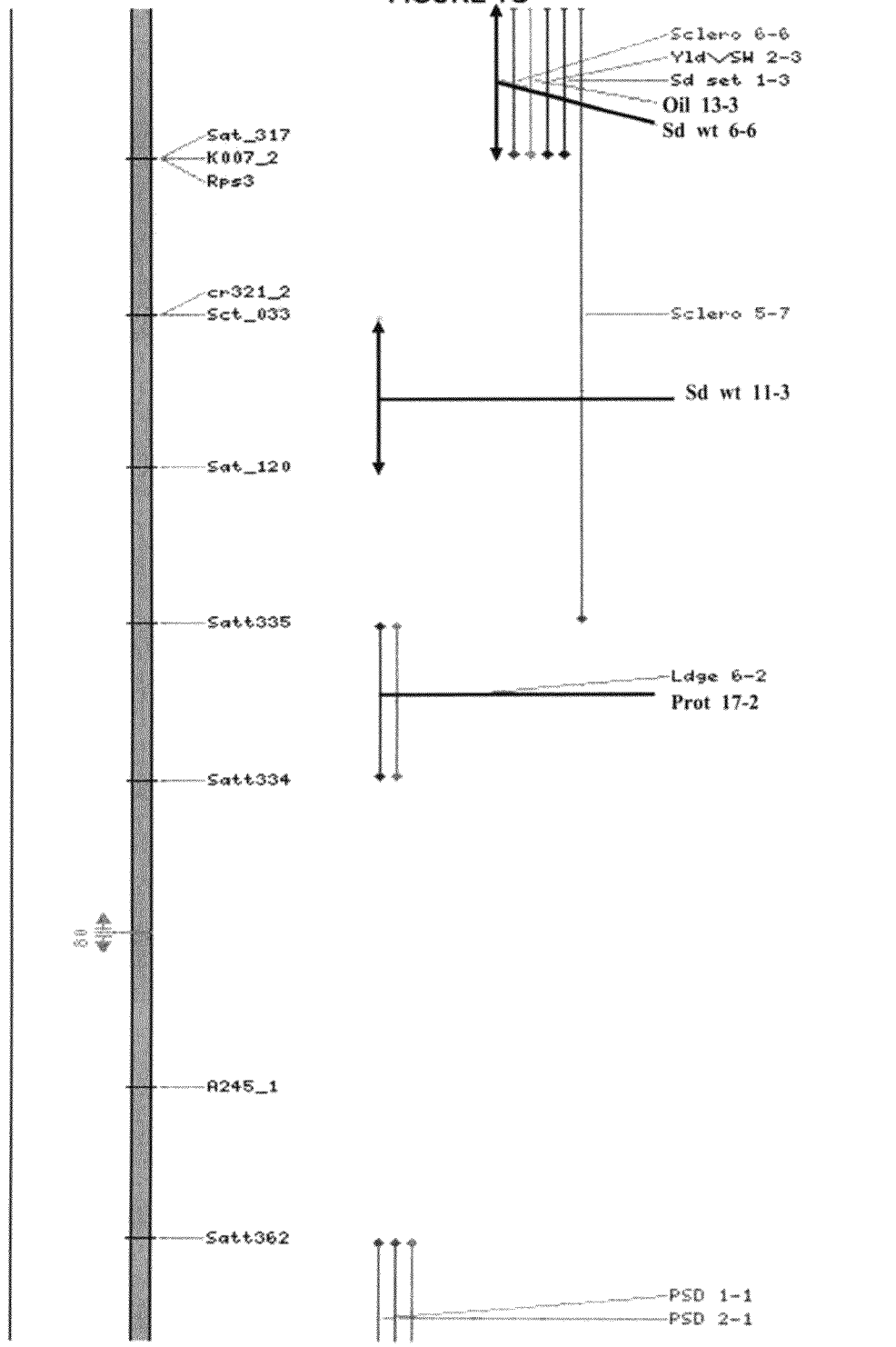

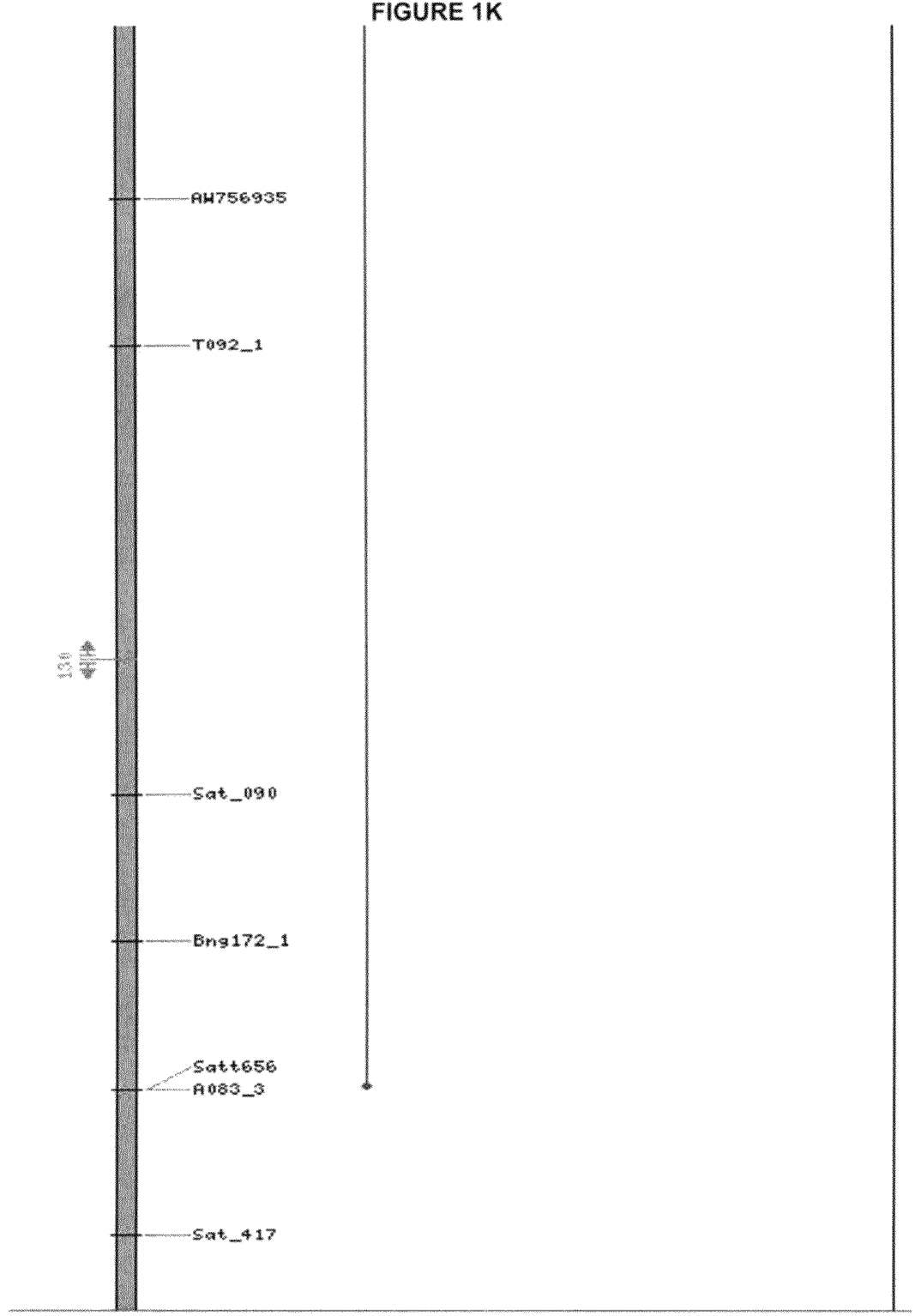

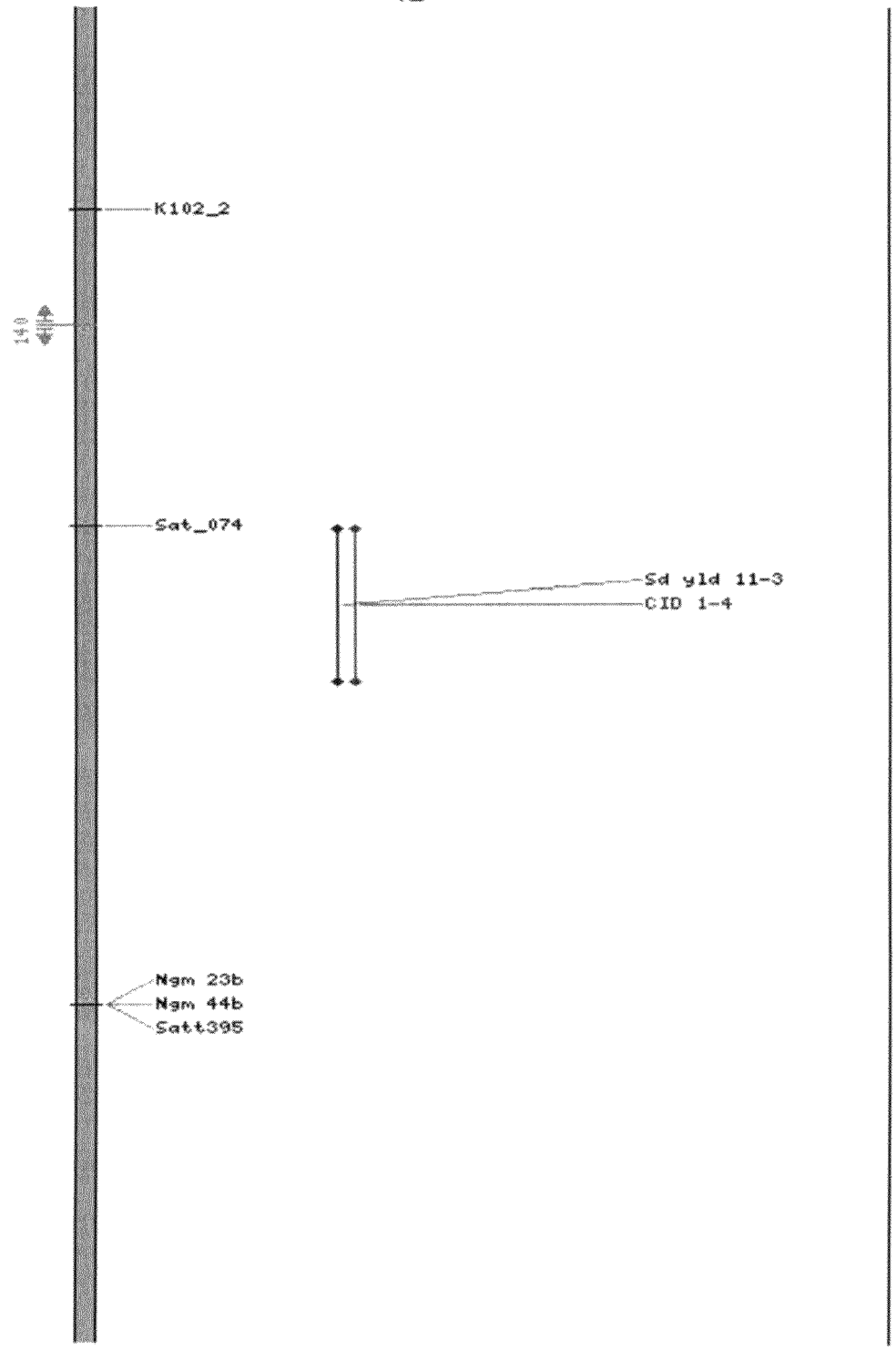

————OPAV06b

- Mag +
0-150.97 cM

Feature Types:
— Gene
— PCR
↕ QTL_fungal
↕ QTL_inorganic
↕ QTL_insect
↕ QTL_leaf-stem
↕ QTL_misc
↕ QTL_nematode
↕ QTL_oil
↕ QTL_other-seed
↕ QTL_pod
↕ QTL_protein
↕ QTL_reprod-period
↕ QTL_whole-plant
↕ QTL_yield
— RAPD
— RFLP
— SSR Menu Symbols:

[i] Map Set Info

[?] Map Details

[M] Matrix View

[X] Delete Map

[F] Flip Map

[N] New Map View

CMap v0.13

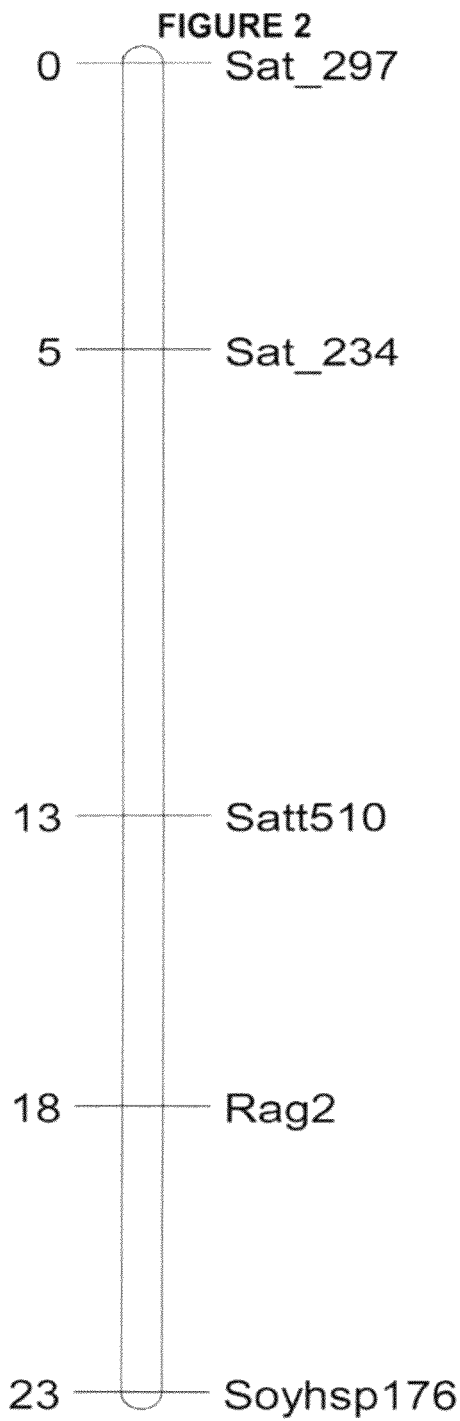

SOYBEAN GENE FOR RESISTANCE TO ALPHIS GLYCINES

CROSS-REFERENCE TO RELATED APPLICATION

This application is a divisional application of U.S. Ser. No. 11/869,500 filed Oct. 9, 2007, now U.S. Pat. No. 7,928,286 issued Apr. 19, 2011, which claims priority to U.S. Provisional Patent Application No. 60/829,123, filed Oct. 11, 2006, both of which prior applications are incorporated herein by reference to the extent not inconsistent herewith.

BACKGROUND

Described herein are a soybean gene for resistance to *Aphis glycines*, soybean plants possessing this gene, which maps to a novel chromosomal locus, and methods for identifying and breeding these plants, the methods involving marker-assisted selection.

Soybeans (*Glycine max* L. Merr.) are a major cash crop and investment commodity in North America and elsewhere. Soybean oil is one of the most widely used edible oils, and soybeans are used worldwide both in animal feed and in human food production.

A native of Asia, the soybean aphid was first found in the Midwest in 2000 (Hartman, G. L. et al., "Occurrence and distribution of *Aphis glycines* on soybeans in Illinois in 2000 and its potential control," (1 Feb. 2001 available at the "plant-managementnetwork" org website). It rapidly spread throughout the region and into other parts of North America (Patterson, J. and Ragsdale, D., "Assessing and managing risk from soybean aphids in the North Central States," (11 Apr. 2002) available at the planthealth.info website in subdirectory soyaphid and further subdirectory aphid02. High aphid populations can reduce crop production directly when their feeding causes severe damage such as stunting, leaf distortion, and reduced pod set (Sun, Z. et al., "Study on the uses of aphid-resistant character in wild soybean. I. Aphid-resistance performance of $F_2$ generation from crosses between cultivated and wild soybeans," (1990) *Soybean Genet. News.* 17:43-48). Yield losses attributed to the aphid in some fields in Minnesota during 2001, where several thousand aphids occurred on individual soybean plants, were >50% (Ostlie, K., "Managing soybean aphid," 2 Oct. 2002) available at the soybeans University of Minnesota website under successive subdirectories crop, insects, aphid, aphid_publication_managingsba with an average loss of 101 to 202 kg ha$^{-1}$ in those fields (Patterson and Ragsdale, supra). In earlier reports from China, soybean yields were reduced up to 52% when there was an average of about 220 aphids per plant (Wang, X. B. et al., "A study on the damage and economic threshold of the soybean aphid at the seedling stage," (1994) *Plant Prot. (China)* 20:12-13) and plant height was decreased by about 210 mm after severe aphid infestation (Wang, X. B. et al., "Study on the effects of the population dynamics of soybean aphid (*Aphis glycines*) on both growth and yield of soybean," (1996) *Soybean Sci.* 15:243-247). An additional threat posed by the aphid is its ability to transmit certain plant viruses to soybean such as Alfalfa mosaic virus, Soybean dwarf virus, and Soybean mosaic virus (Sama, S. et al., "Varietal screening for resistance to the aphid, *Aphis glycines*, in soybean," (1974) *Research Reports* 1968-1974, pp. 171-172; Iwaki, M. et al., "A persistent aphid borne virus of soybean, Indonesian Soybean dwarf virus transmitted by *Aphis glycines*," (1980) *Plant Dis.* 64:1027-1030; Hartman, G. L. et al., supra; Hill, J. H. et al., "First report of transmission of Soybean mosaic virus and Alfalfa mosaic virus by *Aphis glycines* in the New World," (2001) *Plant Dis.* 561; Clark, A. J. and Perry, K. L., "Transmissibility of field isolates of soybean viruses by *Aphis glycines*," (2002) *Plant Dis.* 86:1219-1222).

Because *A. glycines* is a recent pest in the USA, a comprehensive integrated management approach to control the aphid has yet to be developed. Research to evaluate the efficacy of currently-available insecticides and other control measures has just begun.

An integral component of an integrated pest management (IPM) program to control aphids is plant resistance (Auclair, J. L., "Host plant resistance," pp. 225-265 In P. Harrewijn (ed.) *Aphids: Their biology, natural enemies, and control*, Vol. C., Elsevier, New York (1989); Harrewijn, P. and Minks, A. K., "Integrated aphid management: General aspects," pp. 267-272, In A. K. Minks and P. Harrewijn (ed.) *Aphids: Their biology, natural enemies, and control*, Vol. C., Elsevier, New York (1989). Insect resistance can significantly reduce input costs for producers (Luginbill, J. P., "Developing resistant plants—The ideal method of controlling insects," (1969) USDA, ARS. Prod. Res. Rep. 111, USGPO, Washington, D.C. Resistance was reported in *G. soja* (Sun, Z. et al., "Study on the uses of aphid-resistant character in wild soybean. I. Aphid-resistance performance of $F_2$ generation from crosses between cultivated and wild soybeans," (1990) *Soybean Genet. News* 17:43-48), a close relative of *G. max* (Hymowitz, T., "On the domestication of the soybean," (1970) *Econ. Bot.* 24:408-421), and other wild relatives (Zhuang, B. et al., "A study on resistance to soybean mosaic virus and *Aphis glycines* of perennial wild soybean," (1996) *Soybean Genet. Newsl.* 23:66-69). Prior to 2004, there were no reports of resistance in *G. max*. A report from Indonesia had indicated that there was no resistance in a test of 201 soybean cultivars and breeding lines (Sama, S. et al. (1974) Research Reports 1968-1974, p. 171-172. In Varietal screening for resistance to the aphid, *Aphis glycines*, in soybean. Agricultural Cooperation, Indonesia, the Netherlands).

There are numerous examples of the discovery and use of resistance genes to control aphids in crops other than soybean. Examples include Russian wheat aphid (Du Toit, F. (1987), "Resistance in wheat (*Triticum aestivum*) to *Diuraphis noxia* (Homoptera:Aphididae)," *Cereal Res. Commun.* 15:175-179; wheat greenbug (Tyler, J. M., et al. (1985), "Biotype E greenbug resistance in wheat streak mosaic virus-resistant wheat germplasm lines," Crop Science 25:686-688), potato aphid on tomato (Kaloshian, I., et al. (1997), "The impact of Meu-1-mediated resistance in tomato on longevity, fecundity and behavior of the potato aphid," *Macrosiphum euphorbiae*," *Entomol. Exp. Appl.* 83:181-187), and cotton-melon aphid on melon (Klinger, J. et al. (2001), "Mapping of cotton-melon aphid resistance in melon," *J. Am. Soc. Hortic. Ci.* 136:56-63).

A number of soybean markers have been mapped and linkage groups created, as described in Cregan, P. B., et al., "An Integrated Genetic Linkage Map of the Soybean Genome" (1999) Crop Science 39:1464-1490.

U.S. Patent Publication 2006/0014964, Hill, C. B., et al. (2006), "Soybean aphid resistance in soybean Jackson is controlled by a single dominant gene," Crop Science 46:1606-1608, and Hill, C. B., et al. (2006), "A single dominant gene for resistance to the soybean aphid in the soybean cultivar Dowling," Crop Science 46:1601-1605 disclose two previously-discovered soybean aphid resistance genes, Rag$_1$ in Dowling and another gene in Jackson.

A trait that maps to soybean Linkage Group F is root-knot nematode resistance. (Tamulonis, J. P., et al. (1997), "DNA marker analysis of loci conferring resistance to peanut root-knot nematode in soybean," Theor. Appl. Genet. 95:664-670.) Jeong, S. C. et al., "Cloning And Characterization Of An Rga Family From The Soybean Molecular Linkage Group F," in an Abstract published by Plant & Animal Genome VIII Conference, Town & Country Hotel, San Diego, Calif., Jan. 9-12, 2000 at a website address with the usual www prefix followed by intl-pag.org/8/abstracts/pag8255.html and in Yong G. Yu, Glenn R. Buss, and M. A. Saghai Maroof (1996), "Isolation of a superfamily of candidate disease-resistance genes in soybean based on a conserved nucleotide-binding site," PNAS, 93:11751-11756, discloses that the soybean chromosomal region on linkage group F flanked by the markers K644 and B212 contains several virus, bacteria, fungus and nematode resistance genes.

Conventional plant breeding for insect resistance traditionally relied on screening whole plants for resistance directly with live insects and assessing insect population development or plant damage caused by insect feeding, or indirectly with techniques that measure insect feeding behavior, such as Electrical Penetration Graph (EPG). Implementation of these techniques requires a certain amount of time and specialized space, such as in a greenhouse or plant growth room. More efficient and cost-effective molecular genetic and polymerase chain reaction (PCR) techniques, with the development of DNA markers, enable breeders to significantly increase throughput and efficiency in screening plants for traits that are tightly linked to DNA markers, by screening genomic DNA of plants in the laboratory. There are numerous examples of the use of this technology to select plants with certain traits in breeding programs, including insect resistance. Other publications directed to marker-identification of soybean aphid resistance include Li, Y, et al., "Soybean aphid resistance genes in the soybean cultivars Dowling and Jackson map to linkage group M," Molecular Breeding (in press); Hill, C. B., et al. (2006), "Soybean aphid resistance in soybean Jackson is controlled by a single dominant gene," Crop Science 46:1606-1608; Hill, C. B., et al. (2006), "A single dominant gene for resistance to the soybean aphid in the soybean cultivar Dowling," Crop Science 46:1601-1605; Li, Y., et al. (2004) "Effect of three resistant soybean genotypes on the fecundity, mortality, and maturation of soybean aphid (Homoptera:Aphididae)," Journal of Economic Entomology 97:1106-1111; Hill, C. B., et al. (2004) "Resistance to the soybean aphid in soybean germplasm and other legumes," p. 179, World Soybean Research Conference, Foz do Iguassu, PR, Brazil; Hill, C. B., et al. (2004), "Resistance to the soybean aphid in soybean germplasm," Crop Science 44:98-106; and Hill, C. B., et al. (2004), "Resistance of *Glycine* species and various cultivated legumes to the soybean aphid (Homoptera:Aphididae)," Journal of Economic Entomology 97:1071-1077). Additional methods and molecular tools are needed to allow breeding of *A. glycines* resistance into high-yielding *G. max* soybean varieties.

All publications referred to herein are incorporated herein by reference to the extent not inconsistent herewith.

SUMMARY

A method is provided for determining the presence or absence in a soybean germplasm of a gene for resistance to the soybean aphid, *Aphis glycines*. The aphid resistance trait has been found to be closely linked to a number of molecular markers that map to linkage group F. The gene conferring the resistance trait is designated "Rag2" pending approval of the Soybean Genetics Committee. The Rag2 gene was originally discovered in the resistance source Sugao Zairai (PI200538). ("PI" stands for "plant introduction" and this PI number refers to the USDA depositary accession number.) The trait of resistance to *Aphis glycines* is also found in other varieties as described hereafter.

The Rag2 gene, is non-allelic with the Rag1 gene previously found in the soybean cultivar Dowling (Hill, C. B. et al., (2006), "A single dominant gene for resistance to the soybean aphid in the soybean cultivar Dowling," Crop Science 46:1601-1605). Similar to Rag1, when present in soybean plants, the Rag2 gene conditions strong resistance to the soybean aphid by preventing aphid colonization on plants through reduced aphid multiplication, survival, lifespan, and development of nymphs to adults. Expression of resistance is dominant over susceptibility in heterozygous plants containing both forms of the gene. Resistance controlled by Rag2 is effective against all known soybean aphid biotypes.

The location of the Rag2 gene was mapped to linkage group F on the soybean genetic map and it is closely flanked by two DNA markers called simple sequence repeats (SSR), namely Soyhsp176 and Satt510, which are tightly linked to the gene. The tight linkage of the two DNA markers with Rag2 enables soybean breeders to efficiently identify plants that have the soybean aphid resistance gene in progeny of their crosses without having to inoculate plants with aphids.

Use of the technology to identify the presence of the Rag2 gene facilitates and expedites the development of new soybean aphid-resistant cultivars using conventional breeding methods without genetic engineering, by back crossing the Rag2 gene into current, adapted soybean cultivars, converting them to new soybean aphid resistant soybean cultivars. This technology, combined with the technology to identify Rag1 and the related gene covered in U.S. Patent Publication No. 20060015964 enables the development of soybean cultivars with more than one resistance gene to maximize resistance to the soybean aphid.

In accordance with the present method, the Rag2 gene for resistance to *Aphis glycines* co-segregates with molecular markers with which it is linked on linkage group F, most preferably, Satt510 and Soyhsp176. Additional markers that are also useful for identifying the presence of the Rag2 gene include Sat_120, Sat_234, and Sat_297. The Rag2 gene has been found to map to a locus that lies between the markers Satt510 and Soyhsp176. Other markers of linkage group F may also be used to identify the presence or absence of the gene. Preferably flanking markers are used for identifying the presence of the Rag2 gene for marker-assisted breeding. In one embodiment, the markers used map within about 20 cM, and preferably within about 3 cM to about 10 cM of the Rag2 gene locus (which contains the Rag2 gene), or within about 20 cM and preferably within about 3 cM to about 10 cM of Satt510 or Soyhsp176.

The information disclosed herein regarding Rag2 locus is used to aid in the selection of breeding plants, lines and populations containing *Aphis glycines* resistance for use in introgression of this trait into elite soybean germplasm, i.e., germplasm of proven genetic superiority suitable for cultivar release.

Also provided is a method for introgressing a soybean *Aphis glycines* resistance gene into non-resistant soybean germplasm or resistant soybean germplasm that is more or less resistant than that of PI200538. According to the method, nucleic acid markers linked to the Rag2 gene are used to select soybean plants containing a Rag2 locus. Plants so selected have a high probability of expressing the trait *Aphis glycines* resistance. Plants so selected can be used in a soybean breeding program. Through the process of introgression, the Rag2 gene locus is introduced from plants identified using marker-assisted selection into other plants. According to the method, agronomically desirable plants and seeds can be produced containing the Rag2 gene locus from germplasm containing the Rag2 gene.

The Rag2 gene locus is defined as the DNA between flanking markers Satt510 and Soyhsp176.

Particular examples of sources of Rag2 resistance (aphid resistance conferred by the Rag2 gene) are provided by soybean cultivar Sugao Zarai (PI200538) and progeny thereof carrying the Rag2 gene locus.

Also provided herein is a method for producing an inbred soybean plant adapted for conferring, in hybrid combination, *Aphis glycines* resistance. First, donor soybean plants for a parental line containing the Rag2 gene are selected. According to the method, selection can be accomplished via nucleic acid marker-associated selection as explained herein. Selected plant material may come from, among others, an inbred line, a hybrid, a heterogeneous population of soybean plants, or simply an individual plant. According to techniques well known in the art of plant breeding, this donor parental line is crossed with a second parental line. Preferably, the second parental line is high yielding. This cross produces a segregating plant population composed of genetically heterogeneous plants. Plants of the segregating plant population are screened for the Rag2 gene locus. Those plants having the Rag2 gene locus are selected for further breeding until a line is obtained that is homozygous for resistance to *Aphis glycines* at the Rag2 locus. This further breeding may include, among other techniques, additional crosses with other lines, hybrids, backcrossing, or self-crossing. The result is an inbred line of soybean plants that are resistant to *Aphis glycines* and also have other desirable traits from one or more other inbred lines.

The method can also include producing inbred lines having both Rag trait resistance from Rag trait loci on linkage group M as described in U.S. Patent Publication No. 20060015964 (including Rag1 aphid resistance) and Rag2 aphid resistance from linkage group F, as well as traits derived from elite soybean lines. This method comprises crossing soybean plants having Rag2 resistance with soybean plants having Rag1 gene resistance and additional Rag gene resistance conferred by a gene or gene found on linkage group M, and testing for the presence of the aphid resistance traits from both linkage groups F and M using marker-assisted selection, and then making additional crosses with elite lines. As is known in the art, the aphid resistance traits from linkage groups F and M can be stacked in this manner, along with other desirable traits from the elite line(s), into a new soybean cultivar with the intention to increase the durability and effective lifetime of the aphid resistance trait by increasing the difficulty and time for the soybean aphid to produce genetic variants that can overcome both resistance genes.

Soybean plants, seeds, tissue cultures, variants and mutants having *Aphis glycines* resistance produced by the foregoing methods are also provided herein.

BRIEF DESCRIPTION OF THE DRAWINGS

FIG. 2 is a linkage map of a portion of soybean linkage group F (LGF) showing the locations of the soybean aphid resistance gene Rag2. The location of Sat_297 has been designated as 0, measuring from which the location of Rag2 is shown at 18 cM, midway between Satt510 at 13 cM and Soyhsp176 at 23 cM.

DETAILED DESCRIPTION

Figure 1A:
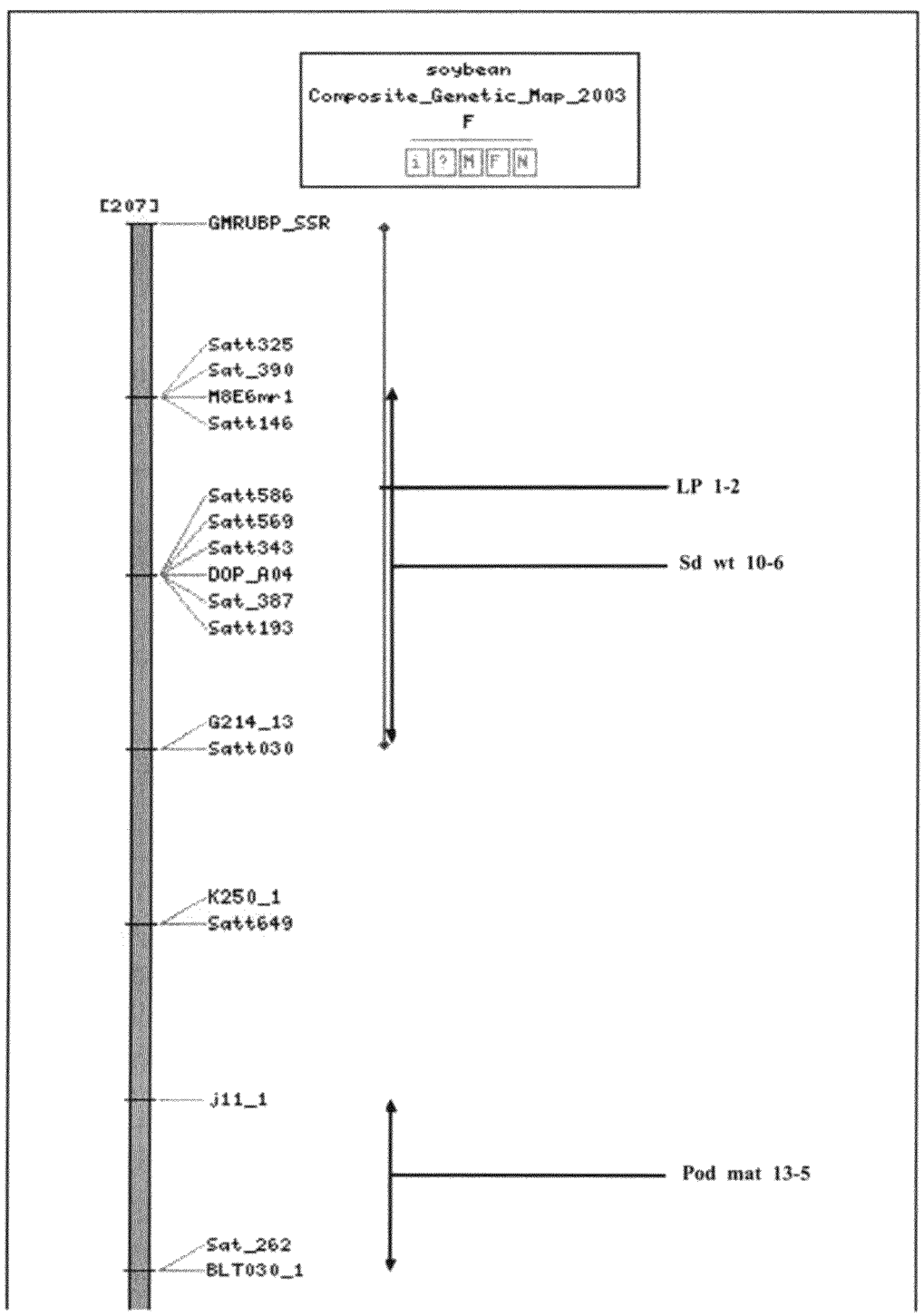
FIG. 1 shows a published soybean genetic linkage F composite map and anchored markers. The map has been broken into thirteen consecutive vertical sections, FIG. 1A through FIG. 1M.
Figure 1B:
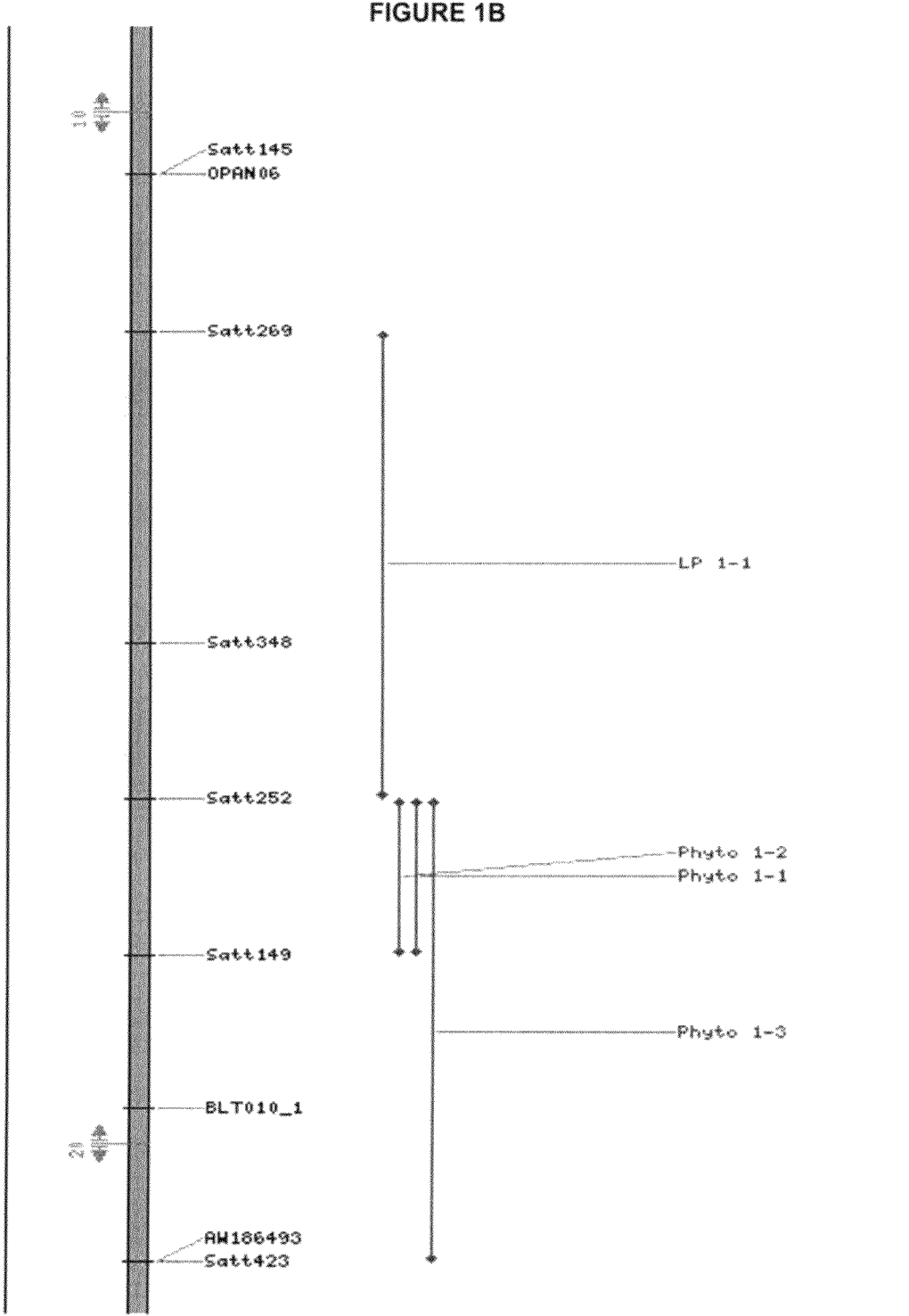
Figure 1C:
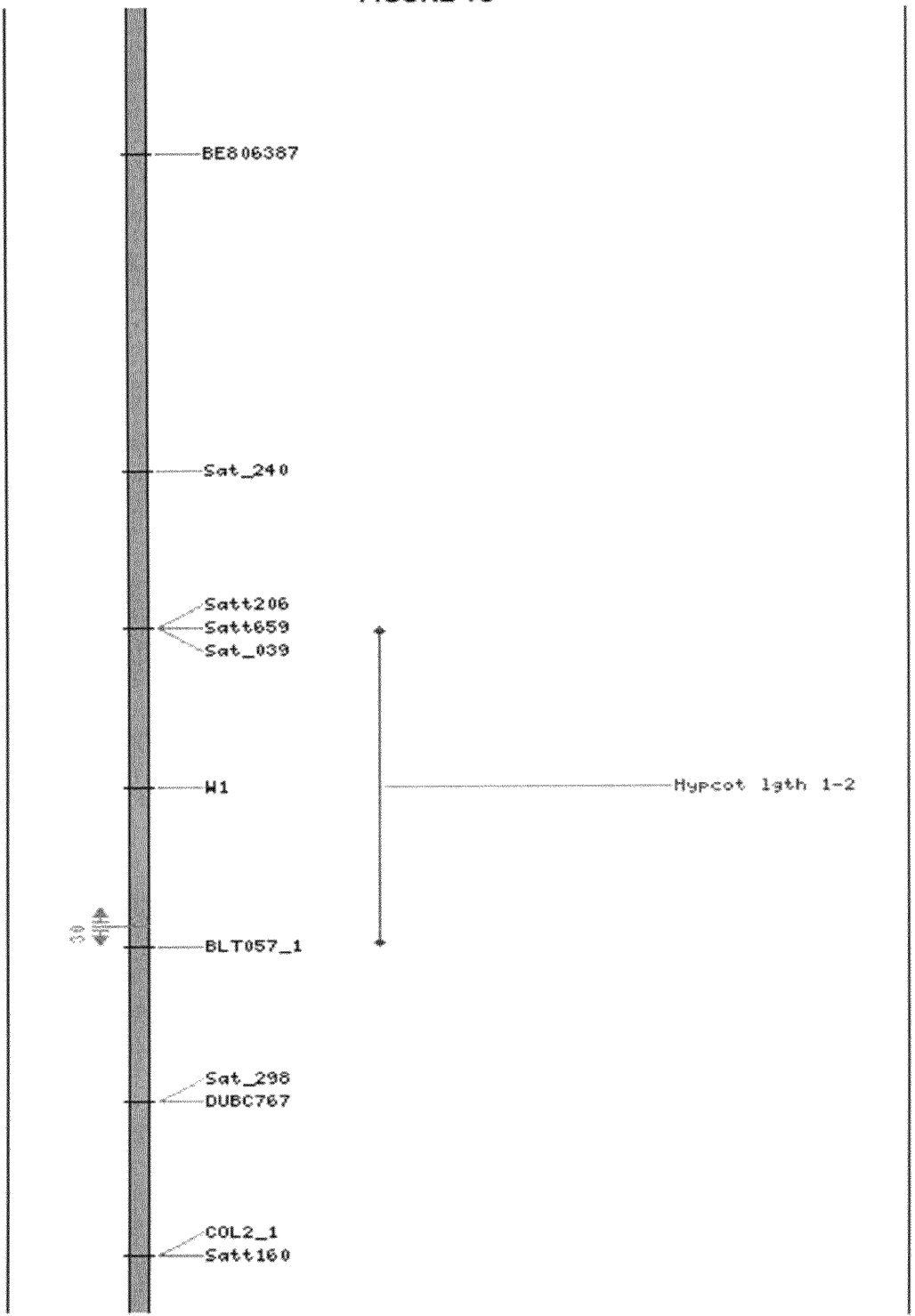
Figure 1F:
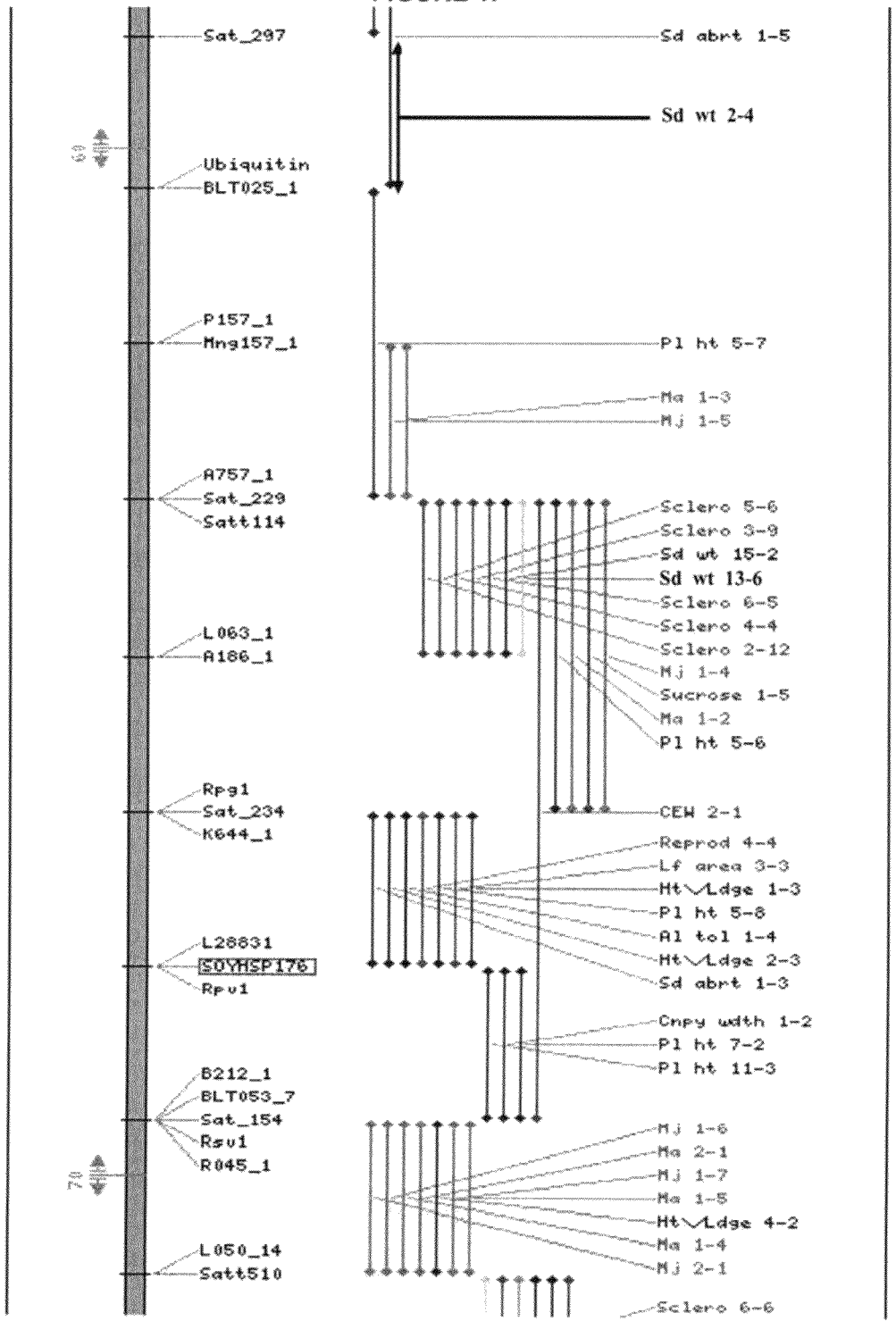
Figure 1H:
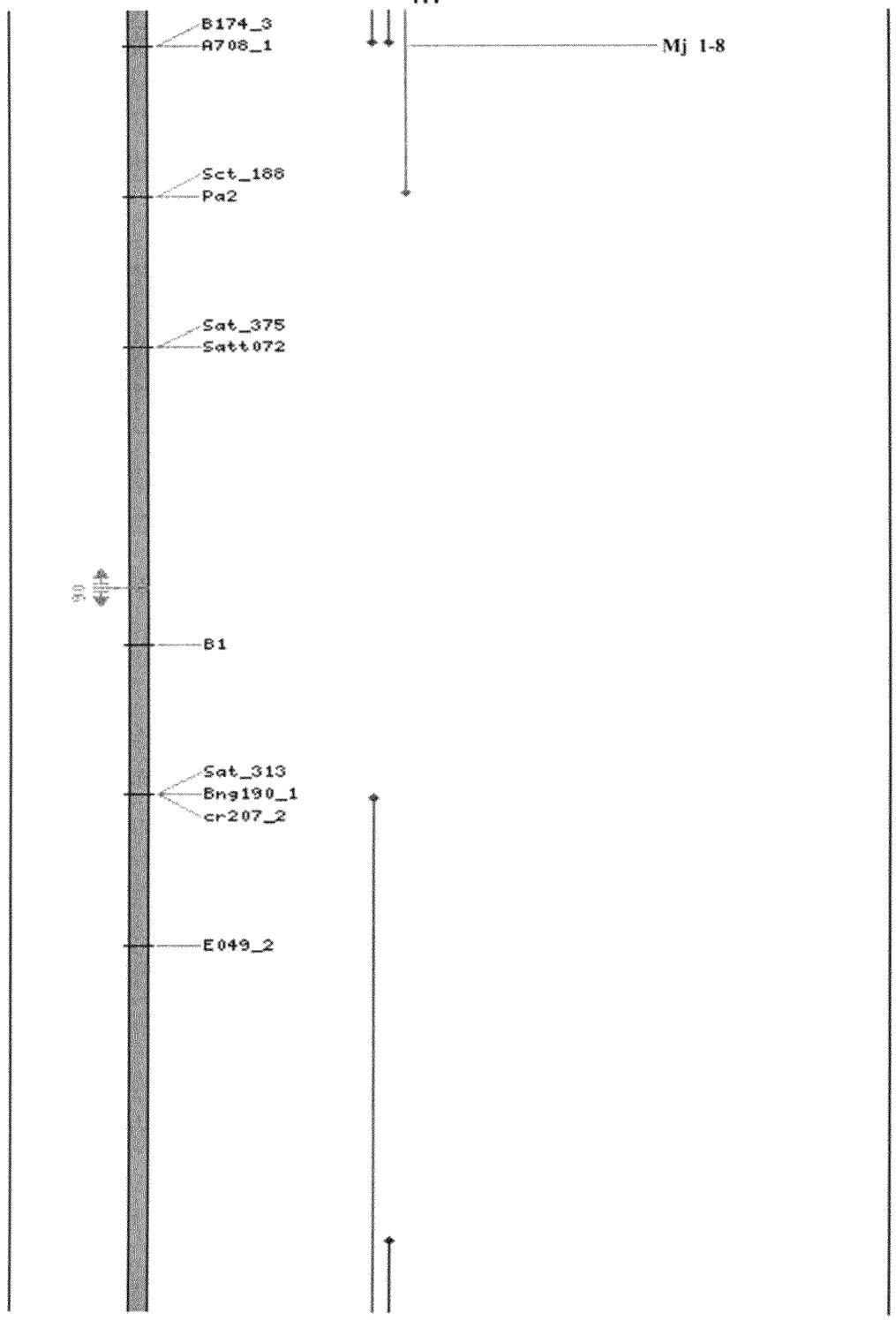
Figure 1I:
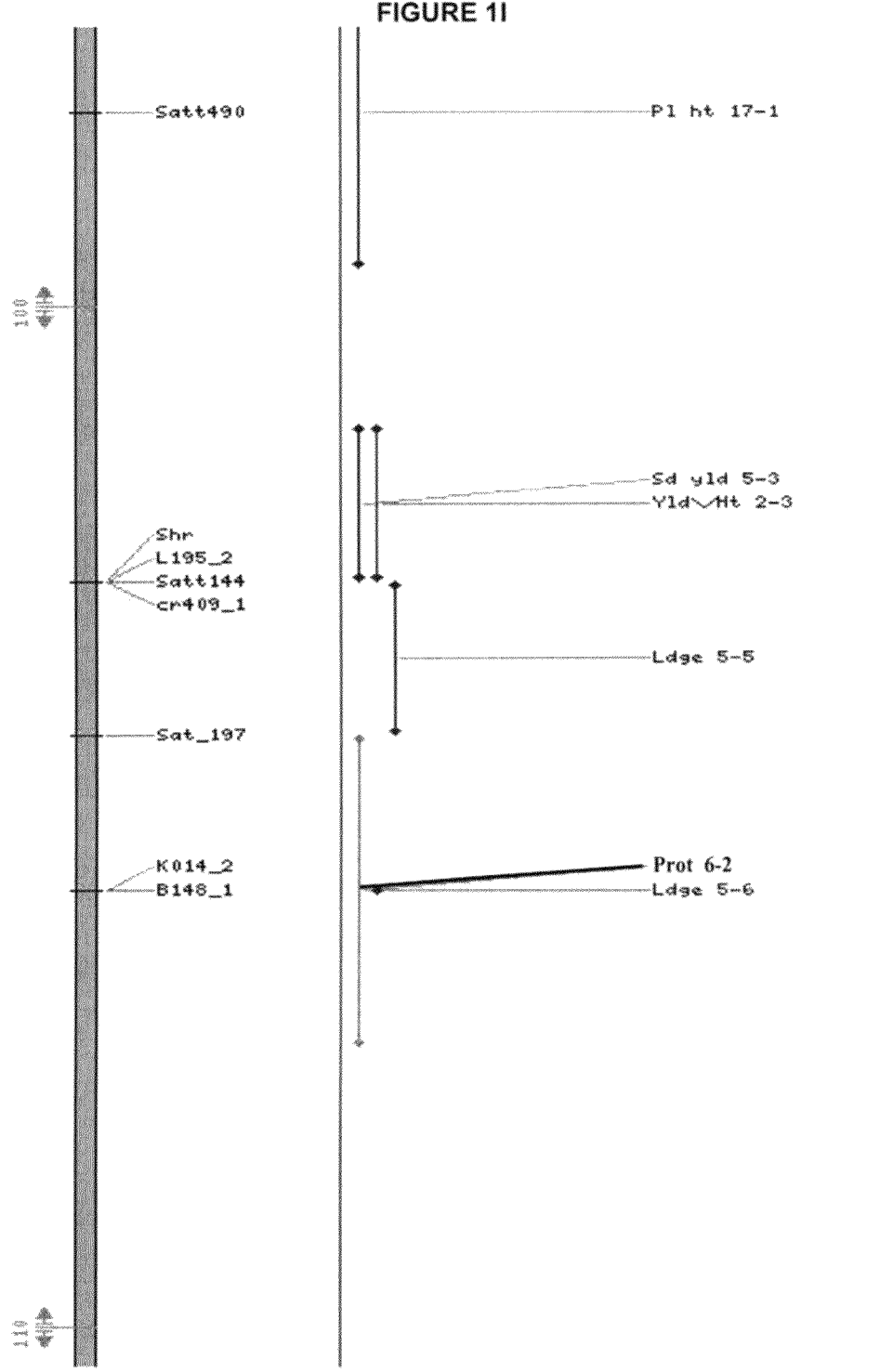
Figure 1J:
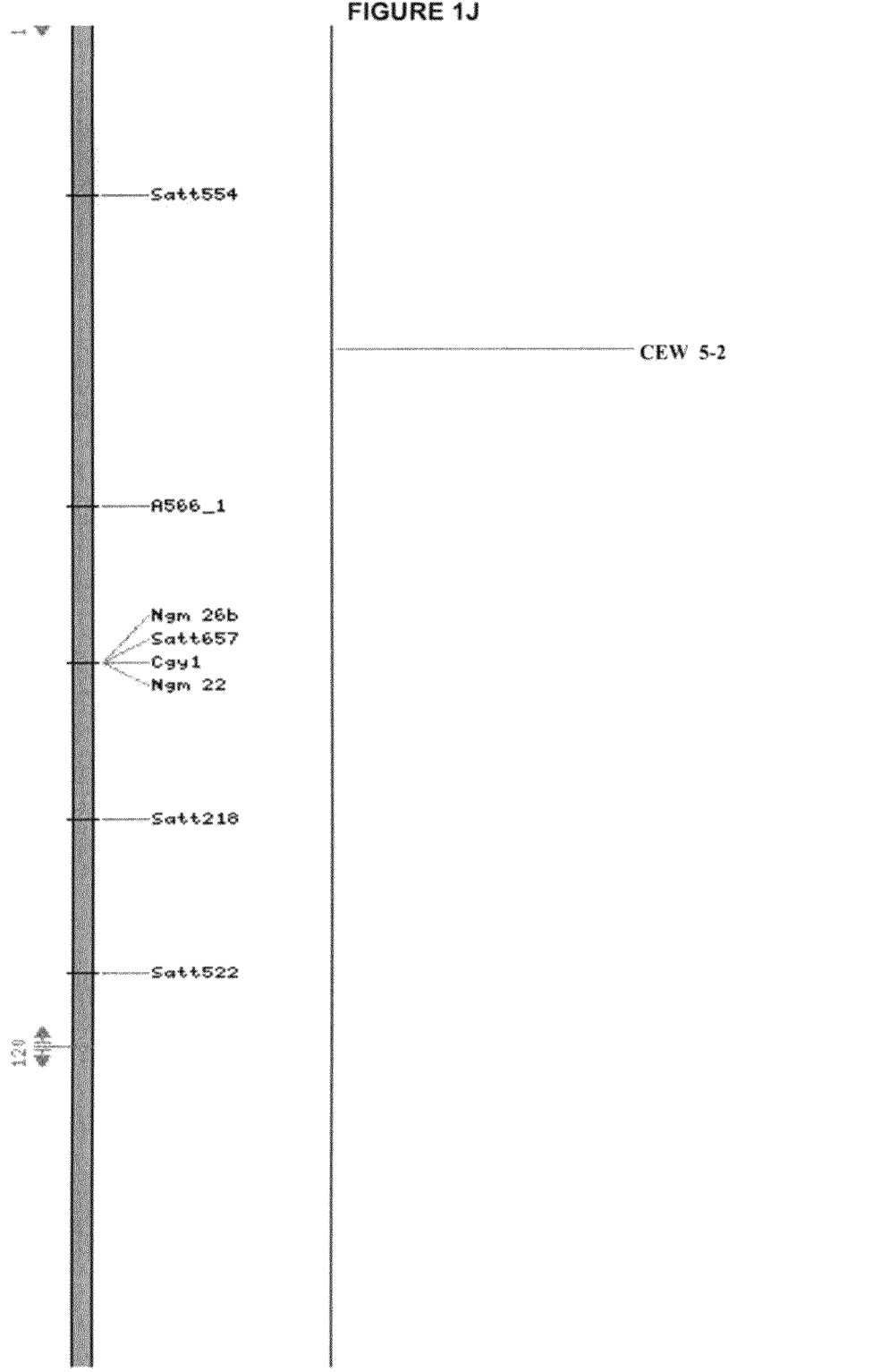
Figure 1M:
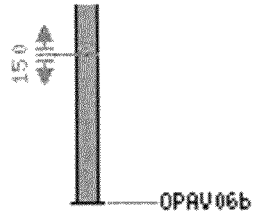

"Allele" is any of one or more alternative forms of a gene, all of which alleles relate to one trait or characteristic. In a diploid cell or organism, the two alleles of a given gene occupy corresponding loci on a pair of homologous chromosomes.

"Backcrossing" is a process through which a breeder repeatedly crosses hybrid progeny back to one of the parents (recurrent parent), for example, a first generation hybrid $F_1$ with one of the parental genotypes of the $F_1$ hybrid.

"Cultivar" and "cultivar" are used synonymously and mean a group of plants within a species (e.g., *Glycine max*) that share certain genetic traits that separate them from the typical form and from other possible varieties within that species. Soybean cultivars are inbred lines produced after several generations of self-pollination. Individuals within a soybean cultivar are homogeneous, nearly genetically identical, with most loci in the homozygous state.

"Gene" means a specific sequence of nucleotides in DNA that is located in the germplasm, usually on a chromosome, and that is the functional unit of inheritance controlling the transmission and expression of one or more traits by specifying the structure of a particular polypeptide or controlling the function of other genetic material. In the present instance, the Rag2 gene for resistance to *Aphis glycines* has been found on major soybean linkage group F flanked by markers Satt510 and Soyhsp176. The Rag2 gene may be isolated by one skilled in the art of genetic manipulation without undue experiments by means known to this art including PCR cloning utilizing the adjacent Satt510 and Soyhsp176 primer sequences, or primer sequences from other markers flanking the gene as described herein, by positional cloning using BACs (bacterial artificial chromosomes), or other methods. See, e.g., Wu, et al., "A BAC and BIBAC-based Physical Map of the Soybean Genome" (2004) Genome Res. February; 14(2):319-26, which describes the use of BACs in mapping the soybean genome. Contiguous BACs lying between Soyhsp176 and Satt510, and in which the Rag2 gene is present, may be found in BAC libraries known to the art, such as The Soybean GBrowse Database.

"Germplasm" means the genetic material with its specific molecular and chemical makeup that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Hybrid plant" means a plant offspring produced by crossing two genetically dissimilar parent plants.

"Inbred plant" means a member of an inbred plant strain that has been highly inbred so that all members of the strain are nearly genetically identical.

"Introgression" means the entry or introduction by hybridization of a gene or trait locus from the genome of one plant into the genome of another plant that lacks such gene or trait locus.

"Molecular marker" is a term used to denote a nucleic acid or amino acid sequence that is sufficiently unique to characterize a specific locus on the genome. Examples include restriction fragment length polymorphisms (RFLPs) and simple sequence repeats (SSRs). RFLP polymorphisms are found when base substitutions, additions, deletions or sequence rearrangements occur between restriction endonuclease recognition sequences. The size and number of fragments generated by one such enzyme is therefore altered. A probe that hybridizes specifically to DNA in the region of such an alteration can be used to rapidly and specifically identify a region of DNA that displays allelic variation between two plant varieties. SSR markers occur where a short sequence displays allelic variation in the number of repeats of that sequence. Sequences flanking the repeated sequence can serve as polymerase chain reaction (PCR) primers. Depending on the number of repeats at a given allele of the locus, the length of the DNA segment generated by PCR will be different in different alleles. The differences in PCR-generated fragment size can be detected by gel electrophoresis. Other types of molecular markers are known. All are used to define a specific locus on the soybean genome. Large numbers of these have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming, requiring growing up of plants to a stage where the trait can be expressed.

Another type of molecular marker is the random amplified polymorphic DNA (RAPD) marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

Another type of molecular marker is the target region amplification polymorphism (TRAP) marker. The TRAP technique employs one fixed primer of known sequence in combination with a random primer to amplify genomic fragments.

A further type of molecular marker is the single nucleotide polymorphism (SNP) marker, in which DNA sequence variations that occur when a single nucleotide (A, T, C, or G) in the genome sequence is altered are mapped to sites on the soybean genome.

Other molecular markers known to the art, as well as phenotypic traits may be used as markers in the methods described herein.

"Linkage" is defined by classical genetics to describe the relationship of traits that co-segregate through a number of generations of crosses. Markers on the same chromosome are linked to one another, meaning that they are inherited as a unit unless there is recombination between markers. Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, the greater the degree of linkage. Traits or markers are considered herein to be linked if they generally co-segregate. A $\frac{1}{100}$ probability of recombination per generation is defined as a map distance of 1.0 centimorgan (1.0 cM). Preferably, markers useful for screening for the presence of Rag2 *Aphis glycines* resistance map to within 20 cM of the trait, and more preferably within 10 cM of the trait.

A second marker that maps to within 20 cM of a first marker that co-segregates with the Rag2 trait and generally co-segregates with the Rag2 trait is considered equivalent to the first marker. Any marker that maps within 20 cM and more preferably 10 cM of the Rag2 trait belongs to the class of preferred markers for use in screening and selection of soybean germplasm having the Rag2 *Aphis glycines* resistance trait. A number of markers are known to the art to belong to linkage group F on which the Rag trait is found. A number of markers are proprietary markers known only to certain of those skilled in the art of soybean plant breeding. A proprietary marker mapping within 20 cM, and preferably within 10 cM, of any publicly known marker specified herein is considered equivalent to that publicly-known marker.

"Linkage group" refers to traits or markers that generally co-segregate. A linkage group generally corresponds to a chromosomal region containing genetic material that encodes the traits or markers.

"Locus" means a chromosomal region where a polymorphic nucleic acid or trait determinant or gene is located.

"Polymorphism" means a change or difference between two related nucleic acids. A "nucleotide polymorphism" refers to a nucleotide that is different in one sequence when compared to a related sequence when the two nucleic acids are aligned for maximal correspondence. A "genetic nucleotide polymorphism" refers to a nucleotide that is different in one sequence when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

"Marker assisted selection" means the process of selecting a desired trait or desired traits in a plant or plants by detecting one or more nucleic acid polymorphisms from the plant, where the nucleic acid polymorphism is linked to the desired trait.

"Plant" means plant cells, plant protoplast, plant cell or tissue culture from which soybean plants can be regenerated, plant calli, plant clumps and plant cells that are intact in plants or parts of plants, such as seeds, pods, flowers, cotyledons, leaves, stems, buds, roots, root tips and the like.

"Probe" means an oligonucleotide or short fragment of DNA designed to be sufficiently complementary to a sequence in a denatured nucleic acid to be probed and to be bound under selected stringency conditions.

"Rag2-derived resistance" means resistance in a soybean germplasm to *Aphis glycines* that is provided by the heterozygous or homozygous expression of the Rag2 gene within the Rag2 locus mapped between the SSR markers Satt510 and Soyhsp176

"Rag phenotype" means resistance to *Aphis glycines* by soybean germplasm, as demonstrated by resistance to *Aphis glycines* after inoculation with same according to the methods described herein. Rag2 phenotype means such aphid resistance conferred by the Rag2 gene.

"Rag soybean plant" means a plant having resistance to *Aphis glycines* that is derived from the presence and expression of at least one Rag gene, or that is shown to have a Rag gene. Rag2 soybean plant means a plant having such aphid resistance conferred by the Rag2 gene.

"Self-crossing or self-pollination" is a process through which a breeder crosses hybrid progeny with itself, for example, a second generation hybrid F$_2$ with itself to yield progeny designated F$_{2:3}$, meaning the progeny from an individual F$_2$ generation plant.

As used herein, the terms "segregate," "segregants," "co-segregate," "hybrid," "crossing," and "selfing" refer to their conventional meanings as understood in the art (see, for instance, Briggs, F. N. and Knowles, P. F. and, *Introduction to Plant Breeding* (Reinhold Publication Corp., New York, N.Y., 1967).

Markers that "flank" the Rag2 gene are markers that occur one to either side of the Rag2 gene. Flanking marker DNA sequences may be part of the gene or may be separate from the gene.

The method for determining the presence or absence of the Rag2 gene, which confers resistance to the soybean aphid *Aphis glycines* in soybean germplasm, comprises analyzing genomic DNA from a soybean germplasm for the presence of at least one molecular marker, wherein at least one molecular marker is linked to the Rag2 trait locus, and wherein the Rag2 trait locus maps to soybean major linkage group F and is associated with resistance to the soybean aphid *Aphis glycines*. The term "is associated with" in this context means that the Rag2 locus containing the Rag2 gene has been found, using marker-assisted analysis, to be present in soybean plants that show or are capable of showing resistance to *Aphis glycines* in live aphid bioassays as described herein.

*Aphis glycines* resistance associated with the Rag2 gene was found in PI200538 and can also occur in the following soybean germplasm accessions that are resistant to all known soybean aphid biotypes: PI71506; PI88508, Showa No. 1-4; PI230977; PI437696, San-haj-hun-mao-huan-dou; PI499955, PI507298, Sokoshin (Kamigoumura); PI518726, Bao jiao huang; PI548237, T260H; PI548409, Sato; PI567391, Jiang se huang dou; PI567541B; PI567598B; 587552, Nan jing da ping ding huang yi 1; PI587617, Jin tan qing zi; PI587656, Huang dou; PI587663, Zhong chun huang dou; PI587666, Er dao zao; PI587669, Zan zi bai; PI587677, Xiao li huang; PI587685, Da li huang 2; PI587693, Yu shan dou; PI587702, Qing pi dou; PI587717, Xiang yang ba yue zha; PI587732, Ying shan ji mu wo; PI587759, Song zi ba yue cha; PI587763, Jing huang 36; PI587775, Tong shan si ji dou; PI587800, Ying shan da li huang; PI587816, Bai mao dou; PI587824, Ying shan qing pi cao; PI587840, Du wo dou; PI587861, Da qing dou; PI587870, Huang pi dou; PI587871, Bao mao dou; PI587873, Feng wo dou; PI587876, Xi mao dou; PI587897, Qing pi dou; PI587899, Ba yue bai; PI587905, Xiao huang dou; PI587972, Chang zi dou; PI588000, Shi yue huang; PI588040, Shan xing dou; PI594421, Da du huang dou; PI594425, Xiao cao huang dou; PI594431, Chang pu qing dou; PI594499, Luo ma aluo; PI594503, Mu gu hei chi huang dou; PI594514, Hua lian dou, PI594554, Huang pi tian dou; PI594573, Lu pi dou; PI594592, Shi yue xiao huang dou; PI594595, Ba yue da huang dou (jia); PI594703, Qing pi dou −1; PI594707, Da hei dou; PI594822, Xi huang dou; PI594868, Huang dou; and PI594879, Huo shao dou. The Rag2 gene can also be found in progeny of the foregoing varieties and in other varieties by methods set forth herein.

Other sources of *A. glycines* resistance include the *G. max* varieties: PI87059, Moyashimame; PI417084A, Kumaji 1; PI508294; PI548445, CNS; PI548480, Palmetto; PI548657, Jackson; PI548663, Dowling; PI567543C; PI567597C; PI587553A; PI587559B, Dan to he shang tou jia; PI587664B, Shan zi bai; PI587668A, Hui mei dou; PI587674A, Ba yue bai; PI587682A, Da li huang 1; PI587684A, Ai jiao huang; PI587686A, Xi li huang 1; PI587687A Xiao li dou 1; PI587700A, Da qing dou; PI587723A, Ying shan ji mu wo; PI587844C, Tong cheng hei se dou; PI587863B, Liu yue bai; PI587877A, Jiu yue zao; PI587891A, Qi yue ba; PI594426A, Tie jiao huang; PI594426B, Tie jiao huang; PI594427A, Ba yuemang; PI594557B, Lao shu dou; PI594560B, Xia shui huang; PI594586A; PI594666B, Liu yue mang 5; PI594711B, Qing huang za dou 3; PI594751A, Long zhou dong feng dou; PI594864, Yang yan dou; PI603521; PI603530A; PI603538A; PI603640; PI603644; PI603655; PI603650; PI605771; PI605823; PI605855; and PI605902, and progeny thereof. *G. soja* varieties: G3; JS1; L4; PI518282, S12 Taichung 38; PI518281, Taichung 37; PI573059, and PI573071 and progeny of these varieties, are also sources of *A. glycines* resistance. These varieties may contain the Rag1 and related aphid resistance gene on linkage group M, and/or can contain the Rag2 gene, or different soybean aphid resistance genes. Resistance that is controlled by Rag1 or Rag2 in these and other varieties can be confirmed by marker-assisted selection as described herein.

Any one of the foregoing varieties or their progeny bearing a Rag gene may be used in the methods described herein, and any combination thereof is considered to be a class of varieties useful in the methods provided herein.

Preferably a marker used to determine the presence or absence of a Rag gene is selected from the group consisting of Satt510, Soyhsp176, Sat_234, Sat_297, and any marker that maps to within at least about 10 to about 20 cM of any of said markers.

Any marker assigned to soybean linkage group F may be useful for this purpose. Exemplary markers of linkage group F include: Satt510, R045_1, Rsv1, Sat_154, BLT053_7, B212_1, Rpv1, Soyhsp176 and L28831, and markers that map within about 3 to about 10 cM, or in another embodiment, within about 10 to about 20 cM, of any of the foregoing.

A further class of markers useful in the present methods include: Ubiquitin, BLT025_1, P157_1, Mng157_1, A757_1, Sat_229, Satt114, L063_1, A186_1, Rpg1, Sat_234, K644_1, L28831, Soyhsp176, Rpv1, B212_1, BLT053_7, Sat_154, Rsv1, R045_1, L050_14, Satt510, Sat_317, K007_2, Rps3, cr321_2, Sct033, Sat_120, Satt335, and Satt334, and markers that map within about 10 to about 20 cM of any of the foregoing.

A further class of markers useful in the present methods include: A401_1, A806_1, K390_1, Sat_309, Satt374, Satt516, Satt425, Mng228_1, Gy5, G248_2, Bng075_1, K002_1, Satt595, B202_1, Sat_133, K265_1, K314_1, Bng004_1, HSP_2, Satt663, Sat 103, Bng118_1, Sat_297, Ubiquitin, BLT025_1, P157_1, Mng157_1, A757_1, Sat_229, Satt114, L063_1, A186_1, Rpg1, Sat_234, K644_1, L28831, Soyhsp176, Rpv1, B212_1, BLT053_7, Sat_154, Rsv1, R045_1, L050_14, Satt510, Sat_317, K007_2, Rps3, cr321_2, Sct033, Sat_120, Satt335, and Satt334, A245_1, Satt362, B174_3, A708_1, Sct_188, Pa2, Sat_375, Satt072, B1, Sat_313, Bng190_1, cr207_2, E049_2, and Satt490, and markers that map within about 10 to about 20 cM of any of the foregoing.

A further class of markers useful in the present methods include: GMRUBP_SSR, Satt325, Sat_390, M8E6mr1, Satt146, Satt586, Satt569, Satt343, DOP_A04, Sat_387, Satt193, G214_13, Satt030, K250_1, Satt649, j11_1, Sat_262, BLT030_1, Satt145, 0PAN06, Satt269, Satt346, Satt252, Satt149, BLT010_1, AW186493, Satt423, BE806387, Sat_240, Satt206, Satt659, Sat_039, W1, BLT057_1, Sat_298, DUBC767, C0L2-1, Satt160, A401_1, A806_1, K390_1, Sat_309, Satt374, Satt516, Satt425, Mng228_1, Gy5, G248_2, Bng075_1, K002_1, Satt595, B202_1, Sat_133, K265_1, K314_1, Bng004_1, HSP_2, Satt663, Sat_103, Bng118_1, Sat_297 Ubiquitin, BLT025_1, P157_1, Mng157_1, A757_1, Sat_229, Satt114, L063_1, A186_1, Rpg1, Sat_234, K644_1, L28831, Soyhsp176, Rpv1, B212_1, BLT053_7, Sat_154, Rsv1, R045_1, L050_14, Satt510, Sat_317, K007_2, Rps3, cr321_2, Sct033, Sat_120, Satt335, and Satt334, A245_1, Satt362, B174_3, A708_1, Sct_188, Pa2, Sat_375, Satt072, B1, Sat_313, Bng190_1, cr207_2, E049_2, SATT490, Shr, L195_2, Satt144, cr409_1, Sat_197, K014_2, B148_1, Sat554, A566_1, Ngm26b, Satt657, Cgy1, Ngm22, Satt218, Satt522, AW756935, T092_1, Sat_090, Bng172_1, Satt656, A083_3, Sat_417, K102_2, Sat_074, Ngm23b, Ngm44b, Satt395, and 0PAV06b, and markers that map within about 10 to about 20 cM of any of the foregoing.

Updated information regarding markers assigned to soybean linkage group F may be found on the USDA's Soybase website. Table 1 provides current information on the Genbank location, location in Linkage Group F, and Accession Nos. of markers useful in the methods disclosed herein. Sequence information pertaining to the markers can be found on Genbank using the gi#. Table 2 provides upper and lower primer sequences for these markers. Note that FIG. 2 indicates a different order for the markers shown. It should be understood that up-to-date information regarding markers on Linkage Group F can be used in the methods disclosed herein as it becomes available.

TABLE 1

Markers on Linkage Group F

| SSR locus | GenBank gi # | cM Position in LG | GenBank Accession # |
| --- | --- | --- | --- |
| GMRUBP | 18741 | 0.00 | V00458 |
| Sat_390 | 31044745 | 1.79 | CC453915 |
| Satt146 | 14969861 | 1.92 | BH126358 |
| Satt325 | 14970019 | 2.23 | BH126516 |
| Satt343 | 14970037 | 3.04 | BH126534 |
| Sat_387 | 31044742 | 3.11 | CC453912 |
| Satt569 | 14970238 | 3.35 | BH126735 |
| Satt193 | 14969903 | 3.42 | BH126400 |
| Satt586 | 14970255 | 3.63 | BH126752 |
| Satt030 | 14969810 | 3.95 | BH126307 |
| Satt649 | 31044834 | 5.36 | CC454004 |
| Sat_262 | 31044627 | 9.69 | CC453797 |
| Satt145 | 14969860 | 10.65 | BH126357 |
| Satt269 | 14969968 | 11.37 | BH126465 |
| Satt348 | 14970041 | 15.29 | BH126538 |

TABLE 1-continued

Markers on Linkage Group F

| SSR locus | GenBank gi # | cM Position in LG | GenBank Accession # |
| --- | --- | --- | --- |
| Satt252 | 14969953 | 16.08 | BH126450 |
| Satt149 | 14969864 | 18.13 | BH126361 |
| Satt423 | 14970105 | 20.56 | BH126602 |
| AW186493 | 6455810 | 21.04 | AW186493 |
| BE806387 | 10237499 | 22.97 | BE806387 |
| Sat_240 | 31044608 | 25.58 | CC453778 |
| Satt659 | 31044844 | 26.71 | CC454014 |
| Satt205 | 14969915 | 26.98 | BH126412 |
| Sat_039 | 15243073 | 27.87 | BH146207 |
| Sat_298 | 31044661 | 32.32 | CC453831 |
| Satt160 | 14969875 | 33.19 | BH126372 |
| Sat_309 | 31044671 | 41.47 | CC453841 |
| Satt374 | 14970064 | 43.01 | BH126561 |
| Satt425 | 14970107 | 43.44 | BH126604 |
| Satt516 | 14970189 | 44.42 | BH126686 |
| Satt595 | 14970264 | 50.24 | BH126761 |
| Sat_133 | 14969806 | 50.78 | BH126303 |
| Satt663 | 31044848 | 56.17 | CC454018 |
| Sat_103 | 14969778 | 57.77 | BH126275 |
| Sat_297 | 31044660 | 59.60 | CC453830 |
| Sat_229 | 31044598 | 62.79 | CC453768 |
| Satt114 | 14969835 | 63.69 | BH126332 |
| Sat_234 | 31044603 | 66.55 | CC453773 |
| SOYHSP176 | 169984 | 68.44 | M11317 |
| Sat_154 | 31044535 | 68.91 | CC453705 |
| Satt510 | 14970184 | 71.41 | BH126681 |
| Sat_317 | 31044678 | 72.97 | CC453848 |
| Sct_033 | 14970276 | 74.13 | BH126773 |
| Sat_120 | 14969793 | 75.97 | BH126290 |
| Satt335 | 14970029 | 77.70 | BH126526 |
| Satt334 | 14970028 | 78.06 | BH126525 |
| Satt362 | 14970053 | 82.83 | BH126550 |
| Sct_188 | 14970285 | 85.33 | BH126782 |
| Satt072 | 14969823 | 87.01 | BH126320 |
| Sat_375 | 31044731 | 88.09 | CC453901 |
| Sat_313 | 31044675 | 91.87 | CC453845 |
| Satt490 | 14970164 | 97.97 | BH126661 |
| Satt144 | 14969859 | 102.08 | BH126356 |
| Sat_197 | 31044568 | 103.51 | CC453738 |
| Satt554 | 14970224 | 111.89 | BH126721 |
| Satt657 | 31044842 | 116.91 | CC454012 |
| Satt218 | 14969925 | 117.65 | BH126422 |
| Satt522 | 14970195 | 119.19 | BH126692 |
| AW756935 | 7686224 | 124.88 | AW756935 |
| Sat_090 | 14969768 | 130.64 | BH126265 |
| Satt656 | 31044841 | 135.12 | CC454011 |
| Sat_417 | 31044771 | 135.95 | CC453941 |
| Sat_074 | 31044511 | 142.35 | CC453681 |
| Satt395 | 14970081 | 146.42 | BH126578 |

TABLE 2

Marker Sequences

| SSR locus | Upper primer sequence (5'-->3') | Lower primer sequence (5-->3') |
| --- | --- | --- |
| GMRUBP | CTGGCGTGCTAAAAGTA [SEQ ID NO: 1] | GGACAGATTTGATCAATAATT [SEQ ID NO: 2] |
| Sat_390 | GCGTAGATGCTTATAATCGACCCTAACAATT [SEQ ID NO: 3] | GCGCGAGGATCCCATAAAAAAAGTAAAATAG [SEQ ID NO: 4] |
| Satt146 | AAGGGATCCCTCAACTGACTG [SEQ ID NO: 5] | GTGGTGGTGGTGAAAACTATTAGAA [SEQ ID NO: 6] |
| Satt325 | GCGGGGTATTAAGGGAAAACAAAA [SEQ ID NO: 7] | GCGTAAACGAACAATCACTTCATA [SEQ ID NO: 8] |
| Satt343 | CATGGCGGAAAGCGAAACA [SEQ ID NO: 9] | TCCCAATTCACCTCTTCA [SEQ ID NO: 10] |

TABLE 2-continued

Marker Sequences

| SSR locus | Upper primer sequence (5'-->3') | Lower primer sequence (5-->3') |
|---|---|---|
| Sat_387 | GCGGAATTTACCAGTTTATAATATTGCTGA [SEQ ID NO: 11] | GCGTACTAAATATTCAAAGACTCAAAGAGAA [SEQ ID NO: 12] |
| Satt569 | GCGCAAATTGCTTCACGCATCCAAAT [SEQ ID NO: 13] | GCGGCCTACTATAGTGAAGGGTATA [SEQ ID NO: 14] |
| Satt193 | GCGTTTCGATAAAAATGTTACACCTC [SEQ ID NO: 15] | TGTTCGCATTATTGATCAAAAAT [SEQ ID NO: 16] |
| Satt586 | GCGGCCTCCAAACTCCAAGTAT [SEQ ID NO: 17] | GCGCCCAAATGATTAATCACTCA [SEQ ID NO: 18] |
| Satt030 | AAAAAGTGAACCAAGCC [SEQ ID NO: 19] | TCTTAAATCTTATGTTGATGC [SEQ ID NO: 20] |
| Satt649 | TTACTGGCCGTGTTTACCCGTGTAA [SEQ ID NO: 21] | GCGGACGTTATAAGATTTTTTTATCATG [SEQ ID NO: 22] |
| Sat_262 | GCGTTTGCATTAGGGATTATCTAGTTTATGA [SEQ ID NO: 23] | GCGGGTTAGAACATTCTTAGTTAGCTCCAG [SEQ ID NO: 24] |
| Satt145 | AGCATATGGGATACAAGTGATTAG [SEQ ID NO: 25] | CGGTGTTGGTGTGGTATGT [SEQ ID NO: 26] |
| Satt269 | GCGTGCCAGGTAGAAAAATATTAG [SEQ ID NO: 27] | GCGGTTTTTCACTTTTCAAAATTC [SEQ ID NO: 28] |
| Satt348 | GCGCTTAGTAATGGTTCCCACAGATAA [SEQ ID NO: 29] | GCGGTGATATCTAGCAACACAA [SEQ ID NO: 30] |
| Satt252 | GCGAATTTGGATTAATTAAATTTATG [SEQ ID NO: 31] | GCGCTCGGTCCTCTCAAATAAGGTCTC [SEQ ID NO: 32] |
| Satt149 | TTGCACATTCTTTTTGGTAAACAGTCATAA [SEQ ID NO: 33] | GTTGGAGGCCATAGTCACATTAATCTTAGA [SEQ ID NO: 34] |
| Satt423 | TTCGCTTGGGTTCAGTTACTT [SEQ ID NO: 35] | GTTGGGGAATTAAAAAAATG [SEQ ID NO: 36] |
| AW186493 | GCGGTGATCCGTGAGATG [SEQ ID NO: 37] | GCGGAAAGTAGCACCAAGAG [SEQ ID NO: 38] |
| BE806387 | GCGACCCCTTTTGTCTTCTT [SEQ ID NO: 39] | GCGGAGGCCAGAGATGAA [SEQ ID NO: 40] |
| Sat_240 | GCGGGCAGAAGTCTAATGAATGTGAAATGA [SEQ ID NO: 41] | GCGGTTGTGACCGAAATAGATGTTATTTAAT [SEQ ID NO: 42] |
| Satt659 | GCGGCTCAACTTCGTGTAACAAG [SEQ ID NO: 43] | GCGCATCGGTAACTATCTAATATTCGTA [SEQ ID NO: 44] |
| Satt206 | GCGCATGTGAAAAGAATGAGATTATGTA [SEQ ID NO: 45] | GCGTCCAAACTCATCCTTAAGGTATT [SEQ ID NO: 46] |
| Sat_039 | CAAGAATAATCTAAAGGTACACTT [SEQ ID NO: 47] | AGTTAAAAAACCCACACAAC [SEQ ID NO: 48] |
| Sat_298 | GCGCGTCGAAGCAAAAATTAAA [SEQ ID NO: 49] | GCGGCGAAACCCACAAAGCATA [SEQ ID NO: 50] |
| Satt160 | TCCCACACAGTTTTCATATAATATA [SEQ ID NO: 51] | CATCAAAAGTTTATAACGTGTAGAT [SEQ ID NO: 52] |
| Sat_309 | GCGAACGGATATATACCCATAAATTTTCATG [SEQ ID NO: 53] | GCGTCATCCAATATAACAATTGTTAAAGTCA [SEQ ID NO: 54] |
| Satt374 | AACATTTGCCGAAAAAAATAACTATGATG [SEQ ID NO: 55] | GCGTATCAATTAAGATCCATTAAGTG [SEQ ID NO: 56] |
| Satt425 | GCGCAATTAAGATCCCTAAGTGATT [SEQ ID NO: 57] | GCGGCTTTTCACTCTTCTTTTATTATT [SEQ ID NO: 58] |
| Satt516 | GCGTTAGCACTATTTTTTTACAAGA [SEQ ID NO: 59] | GCGCCGTTCCTCTTTACTTTAT [SEQ ID NO: 60] |

TABLE 2-continued

Marker Sequences

| SSR locus | Upper primer sequence (5'-->3') | Lower primer sequence (5-->3') |
|---|---|---|
| Satt595 | GATGGGAAGCAAACAAGAAG [SEQ ID NO: 61] | AACCCCCTCCCCTAAAT [SEQ ID NO: 62] |
| Sat_133 | GCGCACATCTTAACTCAAATAATTGATAAAG [SEQ ID NO: 63] | GCGTTCAATTGGATTTGATGAAATTTTAAAT [SEQ ID NO: 64] |
| Satt663 | GCGTCATGCAATGTTGTATAAT [SEQ ID NO: 65] | GCGACTGCAGATAACTTGACTGGTAGT [SEQ ID NO: 66] |
| Sat_103 | ACTGGGAATCCATTTCTTGTTA [SEQ ID NO: 67] | AAAGAACTTTCAATCAAATGTTGTG [SEQ ID NO: 68] |
| Sat_297 | GCGTGAAAATAAATACATAGACATCCACCAT [SEQ ID NO: 69] | GCGTTTTAACACGCATCAACACTCTTC [SEQ ID NO: 70] |
| Sat_229 | GCGTGTGCTACTTCACATCTTGAGAGAAAGA [SEQ ID NO: 71] | GCGAGGGTTTAGAAAAAGATTCACCAAATAT [SEQ ID NO: 72] |
| Satt114 | GGGTTATCCTCCCCAATA [SEQ ID NO: 73] | ATATGGGATGATAAGGTGAAA [SEQ ID NO: 74] |
| Sat_234 | GCGATGCGTTTAATAAGTTTTGAAAAATGCC [SEQ ID NO: 75] | GCGGAAACCATCCTTATATGTCAATTGCTCA [SEQ ID NO: 76] |
| SOYHSP176 | TTTTTGTTTAAGTTACTGTACTGT [SEQ ID NO: 77] | GCTAGTCTTCTACAACCTTCTA [SEQ ID NO: 78] |
| Sat_154 | GCGTCAGGGTCAAGTCATCTAACA [SEQ ID NO: 79] | GCGGACGCATTTCCTATTGATCAAG [SEQ ID NO: 80] |
| Satt510 | GCGAGTTTCGCCGTTACCACCTCAGCTT [SEQ ID NO: 81] | CCCTCTTATTTCACCCTAAGACCTACAA [SEQ ID NO: 82] |
| Sat_317 | GCGACAGTCCCAATACCATTAACAAGT [SEQ ID NO: 83] | GCGTCCTTAGGTACCTAGAATAATTCTTCAC [SEQ ID NO: 84] |
| Sct_033 | CTTTTAAATTATAATAGCATGATCT [SEQ ID NO: 85] | TGCTAATTTAGATTACGTTATGT [SEQ ID NO: 86] |
| Sat_120 | CATATAAAAATGGTCCTCTCACATA [SEQ ID NO: 87] | GCTTGAGCAACTTACAATTCACT [SEQ ID NO: 88] |
| Satt335 | CAAGCTCAAGCCTCACACAT [SEQ ID NO: 89] | TGACCAGAGTCCAAAGTTCATC [SEQ ID NO: 90] |
| Satt334 | GCGTTAAGAATGCATTTATGTTTAGTC [SEQ ID NO: 91] | GCGAGTTTTGGTTGGATTGAGTTG [SEQ ID NO: 92] |
| Satt362 | GCGTTGTTGTTTCAAATGTATTTTAGTT [SEQ ID NO: 93] | GCGGACGGATCATCAAACCAATCAAGAC [SEQ ID NO: 94] |
| Sct_188 | TTCAACCATGTCATAAAAT [SEQ ID NO: 95] | CTCACTCCTCCATAAAAAT [SEQ ID NO: 96] |
| Satt072 | GGAAAGAATCAGCAAAAT [SEQ ID NO: 97] | CCCCCACATAAATAATAAA [SEQ ID NO: 98] |
| Sat_375 | GCGTGTTAATGATTGCATAAGGTTCG [SEQ ID NO: 99] | GCGTGTCAAAAGAAACTCAATAAAGAAAAAT [SEQ ID NO: 100] |
| Sat_313 | GCGTATTCCCTTAACAAAATTAAAGTTTCAC [SEQ ID NO: 101] | GCGCGTCAGCCTAACAAAAAGAATAAAAT [SEQ ID NO: 102] |
| Satt490 | GCGGCACGAGTCAACTTTCTGTTTCCT [SEQ ID NO: 103] | GCGGAAGAAGATTTTCGTTTTTAT [SEQ ID NO: 104] |
| Satt144 | CGTCGCCATCACTATGAGAA [SEQ ID NO: 105] | CCATCTTGAGCAGAGTTTGAAGTT [SEQ ID NO: 106] |
| Sat_197 | GCGATTTTGGTTTTGTTTTATTAG [SEQ ID NO: 107] | GCGGTTAACAGCCAAGTTCTTTC [SEQ ID NO: 108] |
| Satt554 | GCGATATGCTTTGTAAGAAAATTA [SEQ ID NO: 109] | GCGCAAGCCCAAATATTACAAATT [SEQ ID NO: 110] |

TABLE 2-continued

Marker Sequences

| SSR locus | Upper primer sequence (5'-->3') | Lower primer sequence (5-->3') |
|---|---|---|
| Satt657 | GCGCATTTGGACTTTTACTTC [SEQ ID NO: 111] | GCGACGATGTTAATTGGTAGAATC [SEQ ID NO: 112] |
| Satt218 | TCAATCAACAAAAACATAATTCTTC [SEQ ID NO: 113] | ATTTGTGTTTTGTTTTAGCTCTCTA [SEQ ID NO: 114] |
| Satt522 | GCGAAACTGCCTAGGTTAAAA [SEQ ID NO: 115] | TTAGGCGAAATCAACAAT [SEQ ID NO: 116] |
| AW756935 | GCGGCTGGTGATTGTGTAAT [SEQ ID NO: 117] | GCGTAATATAGTTTTGTATTGAAAT [SEQ ID NO: 118] |
| Sat_090 | CTCGCTGCTACTGGTC [SEQ ID NO: 119] | AAGAATGCGTTGGATTTA [SEQ ID NO: 120] |
| Satt656 | GCGTACTAAAAATGGCAATTATTTGTTG [SEQ ID NO: 121] | GCGTGTTTCAGTATTTGGATAATAGAAT [SEQ ID NO: 122] |
| Sat_417 | GCGAATATGGCGTTGAAAATAGTGAT [SEQ ID NO: 123] | GCGACCCAGATTCTGTGCTAAGA [SEQ ID NO: 124] |
| Sat_074 | GGGTGAGAAATACATGCAACTTACA [SEQ ID NO: 125] | GGGCATCAAAATTGATATTAAATGTCTAA [SEQ ID NO: 126] |
| Satt395 | CGCGCTAGTTGAATGAATGT [SEQ ID NO: 127] | GCGCATTGAGGAATTTTTTAT [SEQ ID NO: 128] |

Other types of markers such as SNP markers, for example, as described in Jeong, S. C. and Saghai Maroof, M. A. (2004), "Detection and genotyping of SNPs tightly linked to two disease resistance loci, Rsv1 and Rsv3, of soybean," Plant Breeding 123:305-310, mapping close to Rag2 on linkage group F are also useful in the methods described herein.

Sequences for specific markers useful in the present methods are provided below (taken from the USDA Cregan Soymap website):

Sat_297:

[SEQ ID NO: 129]

```
  1 gatccctca gcctagcctt cagatgtggc ctgaccagag agcattgaat gaacagcacg
 61 ttccttttct tgctccagca ccgtcataca gtggagggat ggttccacct caaggaatgt
121 atccatcttc tgattggagt gggtatcatc aggtaccttt gaatccatat taccctcccg
181 gtgttccttt cccgcatttt ccagctgccc atatgaatca cccgatgtac aaggctgcag
241 ataccagg acatcaacca ccaccatctg atgagtatcc cgagagacct ggccaacctg
301 aatgccagca tttcgtta
```

Sat_234:

[SEQ ID NO: 130]

```
  1 taacgcgaaa gggggaacat cttatatgaa taataataaa tggagaaaag gaaaagaatc
 61 acaggttcca ggttttttcc ttttatccc tccttttctt cctaaattct gaggtttcac
121 cataaccata ttgggatc
```

Soyhsp176:

[SEQ ID NO: 131]

```
  1 gaattctgaa attgggtctt tttgtgggca cttttttgatg ttttttgttta agttactgta
 61 ctgtgggcca caaaacgtat agatcaaagt agtaataata atattgatta aatgatatat
121 atatatatat atatatatat atatctagaa ggttgtagaa gactagctag aacgtacgta
181 ttcgtgtgga gaagtcctga agtttatcga atcatctaaa actgctaaaa tagcaaacaa
241 cattatattg taaacaatat ttttctggaa tatcaagag tatccttttca cttccttttaa
301 atacctcgag tgtccccatt gacatcatca aacaagagaa gagttacaga atttcctgtt
361 tacgatctca ttacaatttt gcaactttca aagcttatta gctaaagtaa catcaaaaga
421 tgtcattgat tccaagtatt ttcggtggcc caaggagcaa cgtgttcgat ccattctcac
481 tcgatatgtg ggatccttc aaggatttc atgttccac ttcttctgtt tctgctgaaa
541 attctgcatt tgtgaacaca cgtgtggatt ggaaggagac ccaagaggca cacgtgctca
601 aggctgatat tccaggcgtg aagaaaggag aagtgaaggt tcagattgaa gatgataggg
661 ttcttcagat tagcggagag aggaacgttg agaaggaaga caagaacgac acgtggcatc
721 gcgtggaccg tagcagtgga aagttcatga gaaggttcag attgccagag aatgcaaaag
781 tggagcaagt aaaaggcttgt atggaaaatg gggttctcac tgttactatt ccaaaggaag
841 aggttaagaa gtctgatgtt aagcctatag aaatctctgg ttaaacttgg tttcactgaa
```

-continued

```
 901 aatcgtgaga gcttttaaat ttgctttgtt gtaataagtg tcctttgtct tgtgttccaa
 961 tggtgatttt gagaaagatc atacaattgt gccttgtgtt gttgtgcaag tgtaattgaa
1021 gtgaataaaa aattaacacc tgctttcaga aaattttgct gtgtgtcatt gtcatcgaat
1081 atgtgatgta ggcaagaaat agaccgtgaa aataatatct gacatttggc taattgcttt
1141 tgttatgctg agacactcta tgtgaaataa ctgcatttat catgttccat cttcttaata
1201 caagaagtca ataccaatgt cttaccaaat taagataaca ggttgatttg gactcatcaa
1261 agtgcagccc tttatttgga ctcatcaaag tgcagcacta aagggttttg ttaactagca
1321 agttcagagc atcatttaag taattaaaag aaaaaatatt aaatatataa atcataagat
1381 gatatcaaaa aattcatgaa cagtctcttc attttttttc aataaaaata tttttatttt
1441 aatttttaa aataatatcc tcataacatt ggtttaactc ccaagtttaa aatttactag
1501 tgctagataa attctctaag ataatgtata gataaaaata agataaatta gaaaattttt
1561 aaggagagat tttttttat aaaaattagg tatatgtatt ggttttagtt tacagagaaa
1621 tataatttat attttctttt tgtgtaaata ttaatgaaaa aaattattca aattcaattc
1681 taaatcttaa tattttttt gacagaattc t
```

Satt510 (BAC-cultivar Faribault):
[SEQ ID NO: 132]

```
  1 gccgtcgcct tagccggagc tgcaggctcc gtgccttgct ccgccgccat
 61 catcggtgcc tcgctcctgt tgtctctcat gactgcgttt gacgttttaa gattctatat
121 atagtttgca tttcatgaat tattattcca aaataatata tagagagata ataaactgtt
181 agattgcgag tttcgccgtt accacctcag cttattttat gattattatt attattatta ttattattat
241 tattattatt attattatta ttattattat tattaattgt tgtaggtctt agggtgaaat aagagggatt
301 ttgatcctct ctacattttt attgttaatt atgtaatgct atatattatg tatgggtata atttagatcc
361 agtcatttta tgtttctcat gttctttttt ttaatttatc acttctataa agaaaataac ttaaactcaa
421 aatacttata ataacatagc tgatacattt atattatatc cactaaatta tttgatatat gagcagtatc
481 gtagtggtat aggtttgaat gtcagagg
```

Sat_120:
[SEQ ID NO: 133]

```
  1 taaagctgca ccagctagca tttccttgat atcaataccc tgcaatgcag ctggaagtaa
 61 acccacagct gacatttctg aagtcctacc accaacccaa tcaaacatag gaaaccgagc
121 taaccatccc tctattctag cagcggtatc caacagagaa ttttcttgag taattgcaac
181 accctgtttt gagaattgca gccctgcatc tctgaaggct ttccgtactt ctagtagacc
241 attgcgggtt tcaggtgtgc ctccgctctt agaaatgaca attacaagag tagttgccag
301 ttcaggtcct agttgagcaa tttgatgatc aatcccagca ggatc
```

Sat_375:
[SEQ ID NO: 134]

```
  1 aatcattaac atataccatt agaatatgtt aatgattgca taaggttcgg gcacccacta
 61 tgcctcttac acatataata tatatatata tatatatata ttttgctgat taaaaaaaaa
121 ctattagaat atgttattct cagtcttagt ttattttaga cttttagatt ttgagtagtt
181 acatattaac attctaaata gtgcaaatac tatattgaaa attcattatt tttctttatt
241 gagtttcttt tgacatatta taattacatt acttagatag actacttata tttctttctg
301 tatatatgat aaggtgtatt actaacccca ctagagctac aactacaact aaagaaataa
361 tataaaacta tgaatatcaa tcttctgtgt tttcatttaa ttatattcgg ttataaaaca
421 ataacagctc ataaaacaat aattattgaa atttaaaatc c
```

Markers that map closer to the Rag2 locus are preferred over markers that map farther from the Rag2 locus for use in the present methods. The markers may be any type of mapped molecular marker or phenotypic trait known to the art, including restriction fragment length polymorphism (RFLP) markers, target region amplification polymorphism (TRAP) markers, random amplified polymorphic (RAPD) markers, simple sequence repeat (SSR) markers, single nucleotide polymorphism (SNP) markers, and isozyme markers.

In one embodiment of the methods described herein, markers flanking the Rag2 locus are used in the marker-assisted selection processes as described herein. The genomic DNA of soybean germplasm is preferably tested for the presence of at least two of the foregoing molecular markers, one on each side of the Rag2 locus. Most preferably, the two markers are Soyhsp176 and Satt510. Markers that map close to Soyhsp176 and Satt510 can also be used, provided they fall to either side of the Rag2 locus. Preferably, one of said at least two molecular markers is within at least about 3 to about 10 cM, or about 10 to about 20 cM of Satt510, and another of said at least two molecular markers is within at least about 3 to about 10 cM or about 10 to about 20 cM of Soyhsp176, and to ensure that the markers used flank the Rag2 locus, one of said at least two molecular markers within at least about to 3 about 10 cM or about 10 to about 20 cM of Satt510 should be farther than that distance from Soyhsp176, and another of said at least two molecular markers within at least about 3 to about 10 cM or about 10 to about 20 cM of Satt510 should be farther than that distance from Soyhsp176.

A method described herein for reliably and predictably introgressing soybean *Aphis glycines* resistance into non-resistant soybean germplasm or into less or differently-resistant soybean germplasm comprises: providing a first soybean germplasm that has Rag2-gene-derived resistance to *Aphis glycines*; providing a second soybean germplasm that lacks Rag2-gene-derived resistance to *Aphis glycines*; crossing the first soybean germplasm with the second soybean germplasm to provide progeny soybean germplasm; screening said progeny germplasm to determine the presence of Rag2-gene-derived resistance to *Aphis glycines*; and selecting progeny that tests positive for the presence of Rag2-gene-derived resistance to *Aphis glycines* as being soybean germplasm into which germplasm having Rag2-gene-derived resistance to *Aphis glycines* has been introgressed.

The second soybean germplasm that lacks Rag2-gene-derived resistance to *Aphis glycines* can be germplasm that lacks resistance to *Aphis glycines* entirely, or can be germplasm that has *Aphis glycines* resistance derived from another source, such as a Rag1 or related gene as described in U.S. Patent Publication No. 2006/0014964.

Preferably, the screening and selection are performed by using marker-assisted selection using a marker on major linkage group F as described above.

The screening and selection can also be performed by exposing plants containing said progeny germplasm to aphids of the species *Aphis glycines* in a live aphid bioassay and selecting those plants showing resistance to aphids (or if the second germplasm already carries *Aphis glycines* resistance from a different gene, selecting those plants showing resistance to an *Aphis glycines* biotype that can overcome resistance that is present in the second germplasm) as containing soybean germplasm into which germplasm having Rag2-gene-derived resistance to *Aphis glycines* has been introgressed. The live aphid assay may be any such assay known to the art, e.g., as described in Hill, C. B., et al., "Resistance to the soybean aphid in soybean germplasm" (2004) Crop Science 44:98-106, Hill, C. B., et al., "Resistance of *Glycine* species and various cultivated legumes to the soybean aphid (Homoptera:Aphididae)" (2004) J. Economic Entomology 97(3)1071-1077, "Li, Y. et al., "Effect of three resistant soybean genotypes on the fecundity, mortality, and maturation of soybean aphid (Homoptera:Aphididae)" (2004) J. Economic Entomology 97(3):1106-1111, Hill, C. B., et al., "A single dominant gene for resistance to the soybean aphid in the soybean cultivar Dowling" (2006) Crop Science 46: 1601-1605, or Hill, C. B., et al. "Soybean aphid resistance in soybean Jackson is controlled by a single dominant gene" (2006) Crop Science 46: 1606-1608, or as described in the Examples hereof. A preferred method includes placing aphid-infested plant parts on vegetative cotyledon (VC) stage plants and rating aphid population and plant damage weekly. As described herein, a 0 to 4 scale, where 0=no aphids present, 1=few solitary live or dead aphids (dead aphid bodies) present, 2=several transient aphids (aphids possibly probing for a suitable feeding site) present with some viviparous aptera surrounded by a few nymphs, 3=dense colonies, and 4=dense colonies accompanied by plant damage, including leaf distortion and stunting, may be used.

The screening and selection may also be done by methods including hybridizing nucleic acid from plants containing progeny germplasm to a nucleic acid fragment comprising a Rag2 gene, and selecting those plants having germplasm that hybridizes to the nucleic acid fragment as having resistance to *Aphis glycines*.

A method described herein for breeding a soybean plant homozygous for the Rag2 *Aphis glycines* resistance gene that is a cultivar adapted for conferring, in hybrid combination with a suitable second inbred, Rag2 resistance to *Aphis glycines*, comprises selecting a first donor parental line possessing the desired Rag2 *Aphis glycines* resistance, said first donor parental line comprising a Rag2 *Aphis glycines* resistance gene located on major linkage group F; crossing the first donor parental line with a second parental line that is generally high yielding in hybrid combination to produce a segregating plant population of genetically heterogenous plants; screening the plants of the segregating plant population for the Rag2 gene; selecting plants from the population having the gene; and breeding by self-crossing the plants containing the gene until a line is obtained that is homozygous for the locus containing the Rag2 gene and adapted for conferring, in hybrid combination with a suitable second inbred, Rag2 resistance to *Aphis glycines*.

The screening and selection are preferably performed by using marker-assisted selection as described above, but may also be performed by live aphid bioassay as described above, selecting those plants showing resistance to aphids as containing soybean germplasm having a Rag gene. When it is known that the only source of aphid resistance in the plant material comes from a plant having Rag2 resistance, it can be concluded that the resistance shown in live aphid bioassays is Rag2 resistance. The screening and selection may also be done by hybridizing nucleic acid from plants containing said progeny germplasm to a nucleic acid fragment comprising the Rag2 gene and selecting those plants whose germplasm hybridizes to the nucleic acid fragment as having an aphid resistance gene.

As the parental line having Rag2 soybean aphid resistance, any soybean line known to the art or disclosed herein as having Rag2 soybean aphid resistance, as described above, may be used. In addition, without undue experimentation, varieties set forth in Table 10 known to have soybean aphid resistance can be tested using marker-assisted analysis as described herein for the presence of the Rag2 gene, thus identifying additional lines for use in the breeding methods described herein.

Also provided herein are soybean plants produced by any of the foregoing methods:

Isolated nucleic acid fragments comprising a Rag2 gene are also provided herein. The nucleic acid fragments comprise at least a portion of nucleic acid belonging to linkage group F, and further comprise nucleotide sequences falling between molecular markers Satt510 and Soyhsp176. They are capable of hybridizing under stringent conditions to nucleic acid of a soybean cultivar having Rag2 resistance to *Aphis glycines*.

Vectors comprising such nucleic acid fragments, expression products of such vectors expressed in a host compatible therewith, antibodies to the expression product (both polyclonal and monoclonal), and antisense nucleic acid to the nucleic acid fragment are also provided herein.

Also provided herein are soybean plants having Rag2 resistance to *Aphis glycines* comprising a Rag2 gene and produced by introgression of DNA containing the gene into a soybean germplasm lacking the gene in its genome, and progeny of said soybean plants.

Seed of a soybean germplasm produced by crossing a soybean cultivar having Rag2 *Aphis glycines* resistance in its genome with a soybean cultivar lacking the Rag2 gene in its genome, and progeny thereof, is also provided herein. Such seed, from BC3 or BC4 generations derived from crosses with aphid resistant Sugao Zairai (PI200538)×Ina or ×Williams 82 $F_2$ plants, is made available through the University of Illinois.

EXAMPLES

Example 1

Genetic Analysis of Rag2 in PI200538

Crosses were made between PI200538 and two susceptible soybean cultivars, Ina and Williams 82. The parents, $F_1$ and $F_2$ plants were tested in a choice test in the greenhouse using the methods described in Hill, C. B., Y. Li, and G. Hartman (2006), "A single dominant gene for resistance to the soybean aphid in the soybean cultivar Dowling," Crop Science 46:1601-1605. Three weeks after infestation, aphid colonization was visually rated using the following scale: 0=no aphids present, 1=few solitary live or dead aphids (dead aphid bodies present), 2=several transient aphids present with some viviparous aptera surrounded by a few nymphs, 3=dense colonies, and 4=dense colonies accompanied by plant damage.

PI200538 plants had ratings of 0, I, or 2 with a rating of 1 being most frequent. Ina and Williams 82 plants had ratings of 3 or 4. Progeny from crosses between PI200538 and the susceptible parents were considered to be resistant with ratings of 0 to 2 and susceptible with ratings of 3 or 4. $F_1$ plants were all resistant to the soybean aphid, indicating that resistance was dominant over susceptibility. $X^2$ analyses on the segregation of $F_2$ plants (Table 3) indicated that a single dominant gene conditioned resistance.

TABLE 3

Genetic analysis of the segregation of $F_2$ plants in two Ina × PI200538 and three Williams 82 × PI200538 $F_2$ populations for resistance to the soybean aphid
Observed $F_2$ segregation

| Cross | $F_2$ Family | Resistant | Susceptible | $X^2$ (3:1) | P |
|---|---|---|---|---|---|
| Ina × PI200538 | 4401 | 39 | 14 | 0.06 | 0.81 |
|  | 4741 | 75 | 23 | 0.12 | 0.73 |
|  | Totals |  |  | 0.18 | 0.91 |
|  | Pooled | 114 | 37 | 0.02 | 0.89 |
|  | Heterogeneity |  |  | 0.16 | 0.69 |
| Williams 82 × PI200538 | 4791 | 88 | 30 | 0.01 | 0.92 |
|  | 4792 | 67 | 19 | 0.39 | 0.53 |
|  | 4793 | 48 | 16 | 0.00 | 1.00 |
|  | Totals |  |  | 0.40 | 0.94 |
|  | Pooled | 155 | 49 | 0.10 | 0.75 |
|  | Heterogeneity |  |  | 0.29 | 0.86 |

$F_{2:3}$ progeny from $F_2$ plants derived from plants in two Ina×PI200538 (Table 5) and three Williams 82×PI200538 (Table 6) $F_2$ populations were evaluated for resistance to the soybean aphid. To have high confidence that all possible susceptible segregants were detected, only $F_{2:3}$ families that had a minimum of 11 viable plants were included in the genetic analysis of $F_2$ plant soybean aphid resistance genotypes. A maximum of 20 $F_3$ plants from an $F_2$ plant were included in the genetic analyses.

TABLE 4

Genetic analysis of the segregation of $F_{2:3}$ families, derived from plants in two Ina × PI200538 $F_2$ populations, for $F_2$ plant soybean aphid resistance genotype

| $F_2$ family | $F_2$ plant phenotype | $F_2$ plant genotype | No. of $F_{2:3}$ families | $X^2$ (1:2:1) | P |
|---|---|---|---|---|---|
| 4401 | Resistant | RR (all $F_{2:3}$ plants resistant) | 4 | | |
|  |  | Rr (resistant and susceptible $F_{2:3}$ plants) | 13 | | |
|  |  | rr (all $F_{2:3}$ plants susceptible) | 0 | | |
|  | Susceptible | RR (all $F_{2:3}$ plants resistant) | 0 | | |
|  |  | Rr (resistant and susceptible $F_{2:3}$ plants) | 0 | | |
|  |  | rr (all $F_{2:3}$ plants susceptible) | 5 | 0.82 | 0.66 |
| 4741 | Resistant | RR (all $F_{2:3}$ plants resistant) | 14 | | |
|  |  | Rr (resistant and susceptible $F_{2:3}$ plants) | 20 | | |
|  |  | rr (all $F_{2:3}$ plants susceptible) | 0 | | |
|  | Susceptible | RR (all $F_{2:3}$ plants resistant) | 0 | | |
|  |  | Rr (resistant and susceptible $F_{2:3}$ plants) | 0 | | |
|  |  | rr (all $F_{2:3}$ plants susceptible) | 5 | 4.18 | 0.12 |
| Totals |  |  |  | 5.00 | 0.08 |
| Pooled |  |  |  | 1.62 | 0.44 |
| Heterogeneity |  |  |  | 3.37 | 0.07 |

TABLE 5

Genetic analysis of the segregation of $F_{2:3}$ families, derived from plants in three Williams 82 × PI200538 $F_2$ populations, for $F_2$ plant soybean aphid resistance genotype

| $F_2$ family | $F_2$ plant phenotype | $F_2$ plant genotype | No. of $F_{2:3}$ families | $X^2$ (1:2:1) | P |
|---|---|---|---|---|---|
| 4791 | Resistant | RR (all $F_{2:3}$ plants resistant) | 17 | | |
|  |  | Rr (resistant and susceptible $F_{2:3}$ plants) | 43 | | |
|  |  | rr (all $F_{2:3}$ plants susceptible) | 0 | | |
|  | Susceptible | RR (all $F_{2:3}$ plants resistant) | 1 | | |
|  |  | Rr (resistant and susceptible $F_{2:3}$ plants) | 0 | | |
|  |  | rr (all $F_{2:3}$ plants susceptible) | 13 | 2.62 | 0.27 |
| 4792 | Resistant | RR (all $F_{2:3}$ plants resistant) | 10 | | |
|  |  | Rr (resistant and susceptible $F_{2:3}$ plants) | 33 | | |
|  |  | rr (all $F_{2:3}$ plants susceptible) | 1 | | |
|  | Susceptible | RR (all $F_{2:3}$ plants resistant) | 0 | | |

TABLE 5-continued

Genetic analysis of the segregation of $F_{2:3}$ families, derived from plants in three Williams 82 × PI200538 $F_2$ populations, for $F_2$ plant soybean aphid resistance genotype

| $F_2$ family | $F_2$ plant phenotype | $F_2$ plant genotype | No. of $F_{2:3}$ families | $X^2$ (1:2:1) | P |
|---|---|---|---|---|---|
| | | Rr (resistant and susceptible $F_{2:3}$ plants) | 0 | | |
| | | rr (all $F_{2:3}$ plants susceptible) | 14 | | |
| | | | | 1.97 | 0.37 |
| 4793 | Resistant | RR (all $F_{2:3}$ plants resistant) | 14 | | |
| | | Rr (resistant and susceptible $F_{2:3}$ plants) | 25 | | |
| | | rr (all $F_{2:3}$ plants susceptible) | 0 | | |
| | Susceptible | RR (all $F_{2:3}$ plants resistant) | 0 | | |
| | | Rr (resistant and susceptible $F_{2:3}$ plants) | 3 | | |
| | | rr (all $F_{2:3}$ plants susceptible) | 7 | | |
| | | | | 3 | 0.22 |
| Totals | | | | 7.59 | 0.06 |
| Pooled | | | | 4.34 | 0.11 |
| Heterogeneity | | | | 3.25 | 0.07 |

Results of the $F_2$ genetic analyses indicated that there was a single, dominant gene in PI200538 that conditioned resistance to the soybean aphid. The results of the $F_3$ genetic analyses for the Ina×PI200538 and Williams×PI200538 crosses supported the single, dominant gene hypothesis.

Crosses were made between the cultivars Dowling, possessing Rag1, and Jackson, that likely also possess Rag1, and PI200538, and their $F_2$ progeny were evaluated for soybean aphid resistance to determine if Rag1 and the gene in PI200538 were allelic or the same gene. Segregation of resistant and susceptible $F_2$ plants significantly fit a 15:1 pattern, expected for the segregation of two different, non-allelic dominant genes (Table 6). The results indicated that the gene in PI200538, tentatively called Rag2, is non-allelic and unique from Rag1.

TABLE 6

Genetic analysis of the segregation of $F_2$ progeny for soybean aphid resistance from crosses between Dowling and PI200538 and Jackson × PI200538 Observed $F_2$ segregation

| Cross | Resistant | Susceptible | $X^2$ (15:1) | P |
|---|---|---|---|---|
| Dowling × PI200538 | 39 | 3 | 0.06 | 0.81 |
| Jackson × PI200538 | 71 | 6 | 0.31 | 0.58 |
| Totals | | | 0.37 | 0.83 |
| Pooled | 110 | 9 | 0.19 | 0.66 |
| Heterogeneity | | | 0.18 | 0.67 |

Example 2

Identification of Linked SSR Markers and Soybean Map Location of Rag2

Subsets of 90 $F_2$ plants were randomly selected from the combined F2 populations of each of the crosses Ina× PI200538 and Williams 82×PI200538 for mapping the location of Rag2 in the soybean genetic map. DNA was extracted from each of the plants in each of the two subsets and polymerase chain reaction (PCR) was carried out using simple sequence repeat (SSR) markers developed by Dr. Perry Cregan, USDA-ARS. The PCR products were evaluated on gels as previously described in: Wang, D. J., et al., (2003), "A low-cost, high-throughput polyacrylamide gel electrophoresis system for genotyping with micro satellite DNA markers," Crop Science 43:1828-1832.

Initial SSR marker screening to identify markers that were polymorphic between the parents of the crosses and that could be associated with the soybean aphid resistance gene was done with genomic DNA extracted from the parents and separate DNA samples from 10 randomly selected susceptible $F_2$ plants that were bulked from each cross subset. In order to minimize the number of soybean SSR markers to screen for polymorphisms and association with resistance, knowledge of the potential association between resistance to aphids and root knot nematodes, as put forward in Hill, C. B., Y. Li, and G. L. Hartman, (2004), "Resistance to the soybean aphid in soybean germplasm," Crop Science 44:98-106 was exploited to select markers from soybean linkage groups (LG) E and F. Genes for resistance to peanut root knot nematode, found in PI200538, were mapped to LGs E and F (Tamulonis, J. P., et al. (1997), "DNA marker analysis of loci conferring resistance to peanut root-knot nematode in soybean," Theoretical and Applied Genetics 95:664-670). Two LG M SSR markers, Satt435 and Satt463, tightly linked to Rag1 (U.S. Patent Publication No. 20060015964), were also included in the screen as a check for genetic allelism between Rag1 and Rag2.

Six LG F SSR markers were found to be polymorphic between Ina and PI200538, associated with soybean aphid resistance, and linked to Rag2. The location of Rag2 in relation to the six SSR markers was generated with Joinmap 3.0, a genetic mapping software application, after entering the genotype data for the six LG F SSR markers, the $F_2$ resistance phenotype data, and available $F_2$ genotype data for each of the 90 $F_2$ plants in the Ina×PI200538 F2 mapping population. Tight linkage of Soyhsp176 and Satt510, both within 5 centimorgans (cM) on opposite sides of Rag2, was shown. With the location of Sat_297 taken as zero, and Rag2 at 18 cM, the additional markers were: Sat_234 at 5 cM, Soyhsp176 at 23 cM; Satt510 at 13 cM; Sat_120 at 26 cM and Sat_375 at 40 cM.

Subsequently, genotype data from 45 F2 plants from a cross between Ina×PI200538 was analyzed. Segregation of markers Sat_120 and Sat_375 did not fit the expected F2 1:2:1 ratio for a co-dominant gene, and therefore were dropped from the linkage data described above. The linkage map resulting from this analysis is shown in FIG. 2.

Example 3

Effectiveness of Rag2 Against Different Soybean Aphid Isolates

A soybean aphid population was found in Ohio that could colonize soybean plants possessing the resistance gene Rag1.

Subsequent tests demonstrated that an isolate from the Ohio soybean aphid population was a biotype that could overcome the resistance expressed by Rag1 in soybean plants, distinguishing it from other soybean aphid isolates. Identification of a soybean aphid biotype that can overcome the resistance gene Rag1. In non-choice tests (Table 7) and choice tests (Table 8), resistance expressed by Rag2 in PI200538 was as effective against the Ohio biotype as an isolate from Illinois.

TABLE 7

Number of aphids per plant 10 and 15 d after infestation with the Ohio and Illinois aphid isolates across two non-choice tests.

| Soybean genotype | 10 days after infestation | | 15 days after infestation | |
|---|---|---|---|---|
| | Illinois Isolate | Ohio Isolate | Illinois Isolate | Ohio Isolate |
| Dowling (Rag1) | 8cd[†] | 146a | 12de | 586ab |
| Williams82 | 231a | 209a | 726a | 574abc |
| LD05-16611 (Rag1) | 10cd | 215a | 774a | 548ab |
| Jackson | 7d | 191a | 11de | 396ab |
| Dwight | 146a | 178a | 363ab | 332b |
| PI567541B | 6abcd | 57b | 5abcde | 82c |
| PI567597C | 31b | 12c | 18d | 7e |
| PI200538 (Rag2) | 8cd | 8cd | 9de | 7e |

[†]Means followed by the same letters in the 10 d after infestation columns or the 15 d after infestation columns are not significantly different by the least significant different test (P = 0.05).

TABLE 8

Number of aphids per plant 10 d after infestation with the Ohio isolate in a choice test.

| Soybean genotype | Number of aphids plant$^{-1}$ 10 days after infestation |
|---|---|
| Dwight | 177a |
| LD05-16611 (Rag1) | 168a |
| Williams82 | 166a |
| Dowling (Rag1) | 156a |
| Jackson | 110b |
| PI567541B | 34c |
| PI567597C | 31cd |
| PI200538 (Rag2) | 22d |

[†]Means followed by the same letters in a column are not significantly different by the least significant different test (P = 0.05).

Results of a preliminary, un-replicated, non-choice test of 11 soybean aphid isolates collected from their primary hosts, *Rhamnus cathartica* and *R. frangula*, at different locations in the central USA, indicated that Rag2 provided effective resistance against all of them in PI200538 (Table 9).

TABLE 9

Number of aphids of 11 soybean aphid isolates on Dowling (Rag1) and PI200538 (Rag2) 7 and 10 days after infestation

| Soybean line | Aphid isolate | Number of aphids (7 days) | Number of aphids (15 days) |
|---|---|---|---|
| Dowling (Rag1) | Black Hawk from *R. cathartica* | 2 | 6 |
| | Black Hawk III from *R. cathartica* | 1 | 1 |
| | Bronson, Michigan from *R. cathartica* | 0 | 0 |
| | Hy 47 & 64, Illinois from *R. cathartica* | 7 | 3 |
| | Irish Hills from *R. cathartica* | 4 | 3 |
| | Jolliette College from *R. cathartica* | 5 | 15 |
| | Pit, Indiana from *R. cathartica* | 18 | 126 |
| | Rock II from *R. cathartica* | 10 | 26 |
| | Secor, Indiana from *R. cathartica* | 0 | 0 |
| | Springfield from *R. frangula* | 17 | 4 |
| | Stratton, Indiana from *R. cathartica* | 8 | 42 |
| PI200538 (Rag2) | Black Hawk from *R. cathartica* | 23 | 82 |
| | Black Hawk III from *R. cathartica* | 1 | 0 |
| | Bronson, Michigan from *R. cathartica* | 0 | 0 |
| | Hy 47 & 64, Illinois from *R. cathartica* | 3 | 3 |
| | Irish Hills from *R. cathartica* | | |
| | Jolliette College from *R. cathartica* | 0 | 0 |
| | Pit, Indiana from *R. cathartica* | 0 | 0 |
| | Rock II from *R. cathartica* | 0 | 0 |
| | Secor, Indiana from *R. cathartica* | 2 | 0 |
| | Springfield from *R. frangula* | 1 | 0 |
| | Stratton, Indiana from *R. cathartica* | 2 | 0 |

Example 4

Soybean Accessions that Possess Rag2

A set of 80 soybean germplasm accessions that were resistant to an Illinois soybean aphid isolate were challenged with the Ohio soybean aphid biotype that can overcome Rag1. The accessions listed in Table 3 had resistance not significantly different from PI200538. It is can therefore be deduced that these accessions also possess Rag2 (or possibly another gene effective against the Ohio biotype but not Rag1.)

TABLE 10

List of soybean accessions that had resistance equal to PI200538 (Rag2) against the Ohio soybean aphid biotype

| PI# | Name | Aphid Rating (0-4) |
|---|---|---|
| 71506 | | 0.0 |
| 88508 | Showa No. 1-4 | 1.7 |
| 200538 | Sugao Zarai | 1.0 |
| 230977 | | 1.3 |
| 437696 | San-haj-hun-mao-huan-dou | 1.0 |
| 499955 | | 1.0 |
| 507298 | Sokoshin Kamigoumura | 1.0 |
| 518726 | Bao jiao huang | 1.0 |
| 548237 | T260H | 1.5 |
| 548409 | Sato | 1.6 |
| 567391 | Jiang se huang dou | 1.7 |
| 567541B | | 1.7 |
| 567598B | | 2.0 |
| 587552 | Nan jing da ping ding huang yi 1 | 1.0 |
| 587617 | Jin tan qing zi | 1.0 |
| 587656 | Huang dou | 1.0 |
| 587663 | Zhong chun huang dou | 1.0 |
| 587666 | Er dao zao | 1.0 |
| 587669 | Zan zi bai | 1.0 |
| 587677 | Xiao li huang | 1.0 |
| 587685 | Da li huang 2 | 1.0 |
| 587693 | Yu shan dou | 1.3 |
| 587702 | Qing pi dou | 1.7 |
| 587717 | Xiang yang ba yue zha | 1.3 |
| 587732 | Ying shan ji mu wo | 1.1 |
| 587759 | Song zi ba yue cha | 1.0 |
| 587763 | Jing huang 36 | 1.1 |
| 587775 | Tong shan si ji dou | 1.0 |

TABLE 10-continued

List of soybean accessions that had resistance equal to PI200538 (Rag2) against the Ohio soybean aphid biotype

| PI# | Name | Aphid Rating (0-4) |
|---|---|---|
| 587800 | Ying shan da li huang | 1.0 |
| 587816 | Bai mao dou | 1.1 |
| 587824 | Ying shan qing pi cao | 1.1 |
| 587840 | Du wo dou | 1.1 |
| 587861 | Da qing dou | 1.3 |
| 587870 | Huang pi dou | 1.3 |
| 587871 | Bao mao dou | 1.0 |
| 587873 | Feng wo dou | 1.7 |
| 587876 | Xi mao dou | 1.0 |
| 587897 | Qing pi dou | 2.1 |
| 587899 | Ba yue bai | 1.0 |
| 587905 | Xiao huang dou | 1.0 |
| 587972 | Chang zi dou | 1.0 |
| 588000 | Shi yue huang | 1.1 |
| 588040 | Shan xing dou | 1.0 |
| 594421 | Da du huang dou | 1.6 |
| 594425 | Xiao cao huang dou | 1.1 |
| 594431 | Chang pu qing dou | 1.1 |
| 594499 | Luo ma aluo | 1.1 |
| 594503 | Mu gu hei chi huang dou | 1.3 |
| 594514 | Hua lian dou | 1.1 |
| 594554 | Huang pi tian dou | 1.1 |
| 594573 | Lu pi dou | 1.0 |
| 594592 | Shi yue xiao huang dou | 1.0 |
| 594595 | Ba yue da huang dou (jia | 1.1 |
| 594703 | Qing pi dou −1 | 1.1 |
| 594707 | Da hei dou | 1.3 |
| 594822 | Xi huang dou | 1.0 |
| 594868 | Huang dou | 1.0 |
| 594879 | Huo shao dou | 1.5 |

Although methods and cultivars have been described in detail for purposes of clarity and understanding, it will be clear to those skilled in the art that equivalent cultivars, markers, and methods may be practiced within the scope of the claims hereof.

The invention claimed is:

1. A method for reliably and predictably introgressing soybean *Aphis glycines* resistance conferred by a Rag2 gene into non-resistant soybean germplasm or less resistant soybean germplasm comprising:
providing a first soybean germplasm that has resistance to *Aphis glycines* conferred by said Rag2 gene;
providing a second soybean germplasm that lacks said resistance;
crossing the first soybean germplasm with the second soybean germplasm to provide progeny soybean germplasm;
analyzing said progeny germplasm by marker-assisted selection (MAS) to:

determine the presence of Rag2 resistance to *Aphis glycines* by detecting a resistance to *Aphis glycines* (Rag2) locus that maps to soybean linkage group F of said soybean germplasm, wherein said Rag2 locus is flanked on opposite sides by markers Soyhsp176 and Satt510, and wherein the Rag2 locus comprises allelic DNA sequences that control resistance to *Aphis glycines*; and determine the presence or absence of said allelic sequences linked to the Rag2 gene coding for resistance to *Aphis glycines* in said germplasm; wherein the presence or absence of said allelic sequences linked to said gene is determined by identifying a region of DNA that displays allelic variation between said first and second soybean germplasm linked to said Rag2 locus; and determining that said gene coding for Rag2 resistance is present in said soybean germplasm when said region of DNA comprises a polymorphism linked to Rag2 resistance and present in PI 200538; and determining that said gene is not present in said germplasm when said region of DNA does not comprise said polymorphism linked to Rag2 resistance and present in PI 200538; and selecting progeny that tests positive for the presence of Rag2 resistance to *Aphis glycines* as being soybean germplasm into which germplasm having Rag2 resistance to *Aphis glycines* has been introgressed.

2. The method of claim 1 wherein said allelic form of DNA is identified by MAS comprising selecting a marker from the group consisting of Satt510, Soyhsp176, Sat_234, and Sat_297 and other markers that map to within 20 cM of any of these markers on linkage group F.

3. The method of claim 1 wherein said second soybean germplasm has resistance to *Aphis glycines* conferred by a gene on soybean linkage group M.

4. The method of claim 1 wherein said second soybean germplasm provides a desirable agronomic trait.

5. The method of claim 1 wherein said second soybean germplasm does not contain a determinant for *Aphis glycines* resistance.

6. The method of claim 1 wherein said first soybean germplasm that has resistance to *Aphis glycines* is germplasm of a cultivar having Rag2 *Aphis glycines* resistance selected from the group consisting of PI200538; PI437696; PI499955; PI507298; PI548237; PI567391; PI587656; PI587669; PI587775; PI587870; PI587871; PI587899; PI587972; PI588000; PI588040; PI594431; PI594499; PI594573; PI594707; PI594822; PI594879; and progeny thereof having Rag2 *Aphis glycines* resistance.

7. The method of claim 6 wherein said soybean germplasm that has resistance to *Aphis glycines* is of PI200538.

8. The method of claim 1 for the production of an inbred soybean cultivar adapted for conferring, in hybrid combination with a suitable second inbred, resistance to *Aphis glycines* conferred by the Rag2 gene locus, wherein said second soybean germplasm is high yielding in hybrid combination with said first soybean germplasm that has said resistance to *Aphis glycines*; comprising the further step of self-crossing the plants that tested positive for the presence of said *Aphis glycines* resistance until a line is obtained that is homozygous for said *Aphis glycines* resistance and adapted for conferring, in hybrid combination with a suitable second inbred, said resistance to *Aphis glycines* resistance conferred by the Rag2 gene locus.

* * * * *

SEQUENCE LISTING

<160> NUMBER OF SEQ ID NOS: 134

<210> SEQ ID NO 1
<211> LENGTH: 17
<212> TYPE: DNA
<213> ORGANISM: Artificial
<220> FEATURE:
<223> OTHER INFORMATION: synthetic construct

<400> SEQUENCE: 1
ctggcgtgct aaaagta                                                    17

<210> SEQ ID NO 2
<211> LENGTH: 21
<212> TYPE: DNA
<213> ORGANISM: Artificial
<220> FEATURE:
<223> OTHER INFORMATION: synthetic construct

<400> SEQUENCE: 2
ggacagattt gatcaataat t                                               21

<210> SEQ ID NO 3
<211> LENGTH: 31
<212> TYPE: DNA
<213> ORGANISM: Artificial
<220> FEATURE:
<223> OTHER INFORMATION: synthetic construct

<400> SEQUENCE: 3
gcgtagatgc ttataatcga ccctaacaat t                                    31

<210> SEQ ID NO 4
<211> LENGTH: 31
<212> TYPE: DNA
<213> ORGANISM: Artificial
<220> FEATURE:
<223> OTHER INFORMATION: synthetic construct

<400> SEQUENCE: 4

```
gcgcgaggat cccataaaaa aagtaaaata g                                         31
```

<210> SEQ ID NO 5
<211> LENGTH: 21
<212> TYPE: DNA
<213> ORGANISM: Artificial
<220> FEATURE:
<223> OTHER INFORMATION: synthetic construct

<400> SEQUENCE: 5

```
aagggatccc tcaactgact g                                                    21
```

<210> SEQ ID NO 6
<211> LENGTH: 25
<212> TYPE: DNA
<213> ORGANISM: Artificial
<220> FEATURE:
<223> OTHER INFORMATION: synthetic construct

<400> SEQUENCE: 6

```
gtggtggtgg tgaaaactat tagaa                                                25
```

<210> SEQ ID NO 7
<211> LENGTH: 24
<212> TYPE: DNA
<213> ORGANISM: Artificial
<220> FEATURE:
<223> OTHER INFORMATION: synthetic construct

<400> SEQUENCE: 7

```
gcggggtatt aagggaaaac aaaa                                                 24
```

<210> SEQ ID NO 8
<211> LENGTH: 24
<212> TYPE: DNA
<213> ORGANISM: Artificial
<220> FEATURE:
<223> OTHER INFORMATION: synthetic construct

<400> SEQUENCE: 8

```
gcgtaaacga acaatcactt cata                                                 24
```

<210> SEQ ID NO 9
<211> LENGTH: 19
<212> TYPE: DNA
<213> ORGANISM: Artificial
<220> FEATURE:
<223> OTHER INFORMATION: synthetic construct

<400> SEQUENCE: 9

```
catggcggaa agcgaaaca                                                       19
```

<210> SEQ ID NO 10
<211> LENGTH: 18
<212> TYPE: DNA
<213> ORGANISM: Artificial
<220> FEATURE:
<223> OTHER INFORMATION: synthetic construct

<400> SEQUENCE: 10

```
tcccaattca cctcttca                                                        18
```

<210> SEQ ID NO 11
<211> LENGTH: 30
<212> TYPE: DNA
<213> ORGANISM: Artificial
<220> FEATURE:

<223> OTHER INFORMATION: synthetic construct

<400> SEQUENCE: 11
gcggaattta ccagtttata atattgctga                30

<210> SEQ ID NO 12
<211> LENGTH: 31
<212> TYPE: DNA
<213> ORGANISM: Artificial
<220> FEATURE:
<223> OTHER INFORMATION: synthetic construct

<400> SEQUENCE: 12
gcgtactaaa tattcaaaga ctcaaagaga a              31

<210> SEQ ID NO 13
<211> LENGTH: 26
<212> TYPE: DNA
<213> ORGANISM: Artificial
<220> FEATURE:
<223> OTHER INFORMATION: synthetic construct

<400> SEQUENCE: 13
gcgcaaattg cttcacgcat ccaaat                    26

<210> SEQ ID NO 14
<211> LENGTH: 25
<212> TYPE: DNA
<213> ORGANISM: Artificial
<220> FEATURE:
<223> OTHER INFORMATION: synthetic construct

<400> SEQUENCE: 14
gcggcctact atagtgaagg gtata                     25

<210> SEQ ID NO 15
<211> LENGTH: 26
<212> TYPE: DNA
<213> ORGANISM: Artificial
<220> FEATURE:
<223> OTHER INFORMATION: synthetic construct

<400> SEQUENCE: 15
gcgtttcgat aaaaatgtta cacctc                    26

<210> SEQ ID NO 16
<211> LENGTH: 23
<212> TYPE: DNA
<213> ORGANISM: Artificial
<220> FEATURE:
<223> OTHER INFORMATION: synthetic construct

<400> SEQUENCE: 16
tgttcgcatt attgatcaaa aat                       23

<210> SEQ ID NO 17
<211> LENGTH: 22
<212> TYPE: DNA
<213> ORGANISM: Artificial
<220> FEATURE:
<223> OTHER INFORMATION: synthetic construct

<400> SEQUENCE: 17
gcggcctcca aactccaagt at                        22

<210> SEQ ID NO 18

```
<211> LENGTH: 23
<212> TYPE: DNA
<213> ORGANISM: Artificial
<220> FEATURE:
<223> OTHER INFORMATION: synthetic construct

<400> SEQUENCE: 18
gcgcccaaat gattaatcac tca                                              23

<210> SEQ ID NO 19
<211> LENGTH: 17
<212> TYPE: DNA
<213> ORGANISM: Artificial
<220> FEATURE:
<223> OTHER INFORMATION: synthetic construct

<400> SEQUENCE: 19
aaaaagtgaa ccaagcc                                                     17

<210> SEQ ID NO 20
<211> LENGTH: 21
<212> TYPE: DNA
<213> ORGANISM: Artificial
<220> FEATURE:
<223> OTHER INFORMATION: synthetic construct

<400> SEQUENCE: 20
tcttaaatct tatgttgatg c                                                21

<210> SEQ ID NO 21
<211> LENGTH: 25
<212> TYPE: DNA
<213> ORGANISM: Artificial
<220> FEATURE:
<223> OTHER INFORMATION: synthetic construct

<400> SEQUENCE: 21
ttactggccg tgtttacccg tgtaa                                            25

<210> SEQ ID NO 22
<211> LENGTH: 28
<212> TYPE: DNA
<213> ORGANISM: Artificial
<220> FEATURE:
<223> OTHER INFORMATION: synthetic construct

<400> SEQUENCE: 22
gcggacgtta taagattttt ttatcatg                                         28

<210> SEQ ID NO 23
<211> LENGTH: 31
<212> TYPE: DNA
<213> ORGANISM: Artificial
<220> FEATURE:
<223> OTHER INFORMATION: synthetic construct

<400> SEQUENCE: 23
gcgtttgcat tagggattat ctagtttatg a                                     31

<210> SEQ ID NO 24
<211> LENGTH: 30
<212> TYPE: DNA
<213> ORGANISM: Artificial
<220> FEATURE:
<223> OTHER INFORMATION: synthetic construct

<400> SEQUENCE: 24
```

```
gcgggttaga acattcttag ttagctccag                                          30

<210> SEQ ID NO 25
<211> LENGTH: 24
<212> TYPE: DNA
<213> ORGANISM: Artificial
<220> FEATURE:
<223> OTHER INFORMATION: synthetic construct

<400> SEQUENCE: 25
agcatatggg atacaagtga ttag                                                24

<210> SEQ ID NO 26
<211> LENGTH: 19
<212> TYPE: DNA
<213> ORGANISM: Artificial
<220> FEATURE:
<223> OTHER INFORMATION: synthetic construct

<400> SEQUENCE: 26
cggtgttggt gtggtatgt                                                      19

<210> SEQ ID NO 27
<211> LENGTH: 24
<212> TYPE: DNA
<213> ORGANISM: Artificial
<220> FEATURE:
<223> OTHER INFORMATION: synthetic construct

<400> SEQUENCE: 27
gcgtgccagg tagaaaaata ttag                                                24

<210> SEQ ID NO 28
<211> LENGTH: 24
<212> TYPE: DNA
<213> ORGANISM: Artificial
<220> FEATURE:
<223> OTHER INFORMATION: synthetic construct

<400> SEQUENCE: 28 gcggttttc acttttcaaa attc                                                 24

<210> SEQ ID NO 29
<211> LENGTH: 27
<212> TYPE: DNA
<213> ORGANISM: Artificial
<220> FEATURE:
<223> OTHER INFORMATION: synthetic construct

<400> SEQUENCE: 29
gcgcttagta atggttccca cagataa                                             27

<210> SEQ ID NO 30
<211> LENGTH: 22
<212> TYPE: DNA
<213> ORGANISM: Artificial
<220> FEATURE:
<223> OTHER INFORMATION: synthetic construct

<400> SEQUENCE: 30
gcggtgatat ctagcaacac aa                                                  22

<210> SEQ ID NO 31
<211> LENGTH: 26
<212> TYPE: DNA
<213> ORGANISM: Artificial
<220> FEATURE:
```

<223> OTHER INFORMATION: synthetic construct

<400> SEQUENCE: 31
gcgaatttgg attaattaaa tttatg                                        26

<210> SEQ ID NO 32
<211> LENGTH: 27
<212> TYPE: DNA
<213> ORGANISM: Artificial
<220> FEATURE:
<223> OTHER INFORMATION: synthetic construct

<400> SEQUENCE: 32
gcgctcggtc ctctcaaata aggtctc                                       27

<210> SEQ ID NO 33
<211> LENGTH: 30
<212> TYPE: DNA
<213> ORGANISM: Artificial
<220> FEATURE:
<223> OTHER INFORMATION: synthetic construct

<400> SEQUENCE: 33
ttgcacattc tttttggtaa acagtcataa                                    30

<210> SEQ ID NO 34
<211> LENGTH: 30
<212> TYPE: DNA
<213> ORGANISM: Artificial
<220> FEATURE:
<223> OTHER INFORMATION: synthetic construct

<400> SEQUENCE: 34
gttggaggcc atagtcacat taatcttaga                                    30

<210> SEQ ID NO 35
<211> LENGTH: 21
<212> TYPE: DNA
<213> ORGANISM: Artificial
<220> FEATURE:
<223> OTHER INFORMATION: synthetic construct

<400> SEQUENCE: 35
ttcgcttggg ttcagttact t                                             21

<210> SEQ ID NO 36
<211> LENGTH: 20
<212> TYPE: DNA
<213> ORGANISM: Artificial
<220> FEATURE:
<223> OTHER INFORMATION: synthetic construct

<400> SEQUENCE: 36
gttggggaat taaaaaaatg                                               20

<210> SEQ ID NO 37
<211> LENGTH: 18
<212> TYPE: DNA
<213> ORGANISM: Artificial
<220> FEATURE:
<223> OTHER INFORMATION: synthetic construct

<400> SEQUENCE: 37
gcggtgatcc gtgagatg                                                 18

<210> SEQ ID NO 38

```
<211> LENGTH: 20
<212> TYPE: DNA
<213> ORGANISM: Artificial
<220> FEATURE:
<223> OTHER INFORMATION: synthetic constuct

<400> SEQUENCE: 38
gcggaaagta gcaccaagag                                                   20

<210> SEQ ID NO 39
<211> LENGTH: 20
<212> TYPE: DNA
<213> ORGANISM: Artificial
<220> FEATURE:
<223> OTHER INFORMATION: synthetic construct

<400> SEQUENCE: 39
gcgacccctt ttgtcttctt                                                   20

<210> SEQ ID NO 40
<211> LENGTH: 18
<212> TYPE: DNA
<213> ORGANISM: Artificial
<220> FEATURE:
<223> OTHER INFORMATION: synthetic construct

<400> SEQUENCE: 40
gcggaggcca gagatgaa                                                     18

<210> SEQ ID NO 41
<211> LENGTH: 30
<212> TYPE: DNA
<213> ORGANISM: Artificial
<220> FEATURE:
<223> OTHER INFORMATION: synthetic construct

<400> SEQUENCE: 41
gcgggcagaa gtctaatgaa tgtgaaatga                                        30

<210> SEQ ID NO 42
<211> LENGTH: 31
<212> TYPE: DNA
<213> ORGANISM: Artificial
<220> FEATURE:
<223> OTHER INFORMATION: synthetic construct

<400> SEQUENCE: 42
gcggttgtga ccgaaataga tgttatttaa t                                      31

<210> SEQ ID NO 43
<211> LENGTH: 23
<212> TYPE: DNA
<213> ORGANISM: Artificial
<220> FEATURE:
<223> OTHER INFORMATION: synthetic construct

<400> SEQUENCE: 43
gcggctcaac ttcgtgtaac aag                                               23

<210> SEQ ID NO 44
<211> LENGTH: 28
<212> TYPE: DNA
<213> ORGANISM: Artificial
<220> FEATURE:
<223> OTHER INFORMATION: synthetic construct

<400> SEQUENCE: 44
```

```
gcgcatcggt aactatctaa tattcgta                                         28
```

<210> SEQ ID NO 45
<211> LENGTH: 28
<212> TYPE: DNA
<213> ORGANISM: Artificial
<220> FEATURE:
<223> OTHER INFORMATION: synthetic construct

<400> SEQUENCE: 45

```
gcgcatgtga aagaatgag attatgta                                          28
```

<210> SEQ ID NO 46
<211> LENGTH: 26
<212> TYPE: DNA
<213> ORGANISM: Artificial
<220> FEATURE:
<223> OTHER INFORMATION: synthetic construct

<400> SEQUENCE: 46

```
gcgtccaaac tcatccttaa ggtatt                                           26
```

<210> SEQ ID NO 47
<211> LENGTH: 24
<212> TYPE: DNA
<213> ORGANISM: Artificial
<220> FEATURE:
<223> OTHER INFORMATION: synthetic construct

<400> SEQUENCE: 47

```
caagaataat ctaaaggtac actt                                             24
```

<210> SEQ ID NO 48
<211> LENGTH: 20
<212> TYPE: DNA
<213> ORGANISM: Artificial
<220> FEATURE:
<223> OTHER INFORMATION: synthetic construct

<400> SEQUENCE: 48

```
agttaaaaaa cccacacaac                                                  20
```

<210> SEQ ID NO 49
<211> LENGTH: 22
<212> TYPE: DNA
<213> ORGANISM: Artificial
<220> FEATURE:
<223> OTHER INFORMATION: synthetic construct

<400> SEQUENCE: 49

```
gcgcgtcgaa gcaaaaatta aa                                               22
```

<210> SEQ ID NO 50
<211> LENGTH: 22
<212> TYPE: DNA
<213> ORGANISM: Artificial
<220> FEATURE:
<223> OTHER INFORMATION: synthetic construct

<400> SEQUENCE: 50

```
gcggcgaaac ccacaaagca ta                                               22
```

<210> SEQ ID NO 51
<211> LENGTH: 25
<212> TYPE: DNA
<213> ORGANISM: Artificial
<220> FEATURE:

<223> OTHER INFORMATION: synthetic construct

<400> SEQUENCE: 51
tcccacacag ttttcatata atata                                    25

<210> SEQ ID NO 52
<211> LENGTH: 25
<212> TYPE: DNA
<213> ORGANISM: Artificial
<220> FEATURE:
<223> OTHER INFORMATION: synthetic construct

<400> SEQUENCE: 52
catcaaaagt ttataacgtg tagat                                    25

<210> SEQ ID NO 53
<211> LENGTH: 31
<212> TYPE: DNA
<213> ORGANISM: Artificial
<220> FEATURE:
<223> OTHER INFORMATION: synthetic construct

<400> SEQUENCE: 53
gcgaacggat atatacccat aaattttcat g                             31

<210> SEQ ID NO 54
<211> LENGTH: 31
<212> TYPE: DNA
<213> ORGANISM: Artificial
<220> FEATURE:
<223> OTHER INFORMATION: synthetic construct

<400> SEQUENCE: 54
gcgtcatcca atataacaat tgttaaagtc a                             31

<210> SEQ ID NO 55
<211> LENGTH: 29
<212> TYPE: DNA
<213> ORGANISM: Artificial
<220> FEATURE:
<223> OTHER INFORMATION: synthetic construct

<400> SEQUENCE: 55
aacatttgcc gaaaaaaata actatgatg                                29

<210> SEQ ID NO 56
<211> LENGTH: 26
<212> TYPE: DNA
<213> ORGANISM: Artificial
<220> FEATURE:
<223> OTHER INFORMATION: synthetic construct

<400> SEQUENCE: 56
gcgtatcaat taagatccat taagtg                                   26

<210> SEQ ID NO 57
<211> LENGTH: 26
<212> TYPE: DNA
<213> ORGANISM: Artificial
<220> FEATURE:
<223> OTHER INFORMATION: synthetic construct

<400> SEQUENCE: 57
gcgcaattaa gatccactaa gtgatt                                   26

<210> SEQ ID NO 58

```
<211> LENGTH: 27
<212> TYPE: DNA
<213> ORGANISM: Artificial
<220> FEATURE:
<223> OTHER INFORMATION: synthetic construct

<400> SEQUENCE: 58
gcggcttttc actcttcttt tattatt                                         27

<210> SEQ ID NO 59
<211> LENGTH: 25
<212> TYPE: DNA
<213> ORGANISM: Artificial
<220> FEATURE:
<223> OTHER INFORMATION: synthetic construct

<400> SEQUENCE: 59
gcgttagcac tatttttta caaga                                            25

<210> SEQ ID NO 60
<211> LENGTH: 22
<212> TYPE: DNA
<213> ORGANISM: Artificial
<220> FEATURE:
<223> OTHER INFORMATION: synthetic construct

<400> SEQUENCE: 60
gcgccgttcc tctttacttt at                                              22

<210> SEQ ID NO 61
<211> LENGTH: 20
<212> TYPE: DNA
<213> ORGANISM: Artificial
<220> FEATURE:
<223> OTHER INFORMATION: synthetic construct

<400> SEQUENCE: 61
gatgggaagc aaacaagaag                                                 20

<210> SEQ ID NO 62
<211> LENGTH: 17
<212> TYPE: DNA
<213> ORGANISM: Artificial
<220> FEATURE:
<223> OTHER INFORMATION: synthetic construct

<400> SEQUENCE: 62
aaccccctcc cctaaat                                                    17

<210> SEQ ID NO 63
<211> LENGTH: 31
<212> TYPE: DNA
<213> ORGANISM: Artificial
<220> FEATURE:
<223> OTHER INFORMATION: synthetic construct

<400> SEQUENCE: 63
gcgcacatct taactcaaat aattgataaa g                                    31

<210> SEQ ID NO 64
<211> LENGTH: 31
<212> TYPE: DNA
<213> ORGANISM: Artificial
<220> FEATURE:
<223> OTHER INFORMATION: synthetic construct

<400> SEQUENCE: 64
```

```
gcgttcaatt ggatttgatg aaattttaaa t                                    31

<210> SEQ ID NO 65
<211> LENGTH: 22
<212> TYPE: DNA
<213> ORGANISM: Artificial
<220> FEATURE:
<223> OTHER INFORMATION: synthetic construct

<400> SEQUENCE: 65
gcgtcatgca atgttgtata at                                              22

<210> SEQ ID NO 66
<211> LENGTH: 27
<212> TYPE: DNA
<213> ORGANISM: Artificial
<220> FEATURE:
<223> OTHER INFORMATION: synthetic construct

<400> SEQUENCE: 66
gcgactgcag ataacttgac tggtagt                                         27

<210> SEQ ID NO 67
<211> LENGTH: 22
<212> TYPE: DNA
<213> ORGANISM: Artificial
<220> FEATURE:
<223> OTHER INFORMATION: synthetic construct

<400> SEQUENCE: 67
actgggaatc catttcttgt ta                                              22

<210> SEQ ID NO 68
<211> LENGTH: 25
<212> TYPE: DNA
<213> ORGANISM: Artificial
<220> FEATURE:
<223> OTHER INFORMATION: synthetic construct

<400> SEQUENCE: 68
aaagaacttt caatcaaatg ttgtg                                           25

<210> SEQ ID NO 69
<211> LENGTH: 31
<212> TYPE: DNA
<213> ORGANISM: Artificial
<220> FEATURE:
<223> OTHER INFORMATION: synthetic construct

<400> SEQUENCE: 69
gcgtgaaaat aaatacatag acatccacca t                                    31

<210> SEQ ID NO 70
<211> LENGTH: 27
<212> TYPE: DNA
<213> ORGANISM: Artificial
<220> FEATURE:
<223> OTHER INFORMATION: synthetic contruct

<400> SEQUENCE: 70
gcgttttaac acgcatcaac actcttc                                         27

<210> SEQ ID NO 71
<211> LENGTH: 31
<212> TYPE: DNA
<213> ORGANISM: Artificial
<220> FEATURE:
```

<223> OTHER INFORMATION: synthetic construct

<400> SEQUENCE: 71
gcgtgtgcta cttcacatct tgagagaaag a         31

<210> SEQ ID NO 72
<211> LENGTH: 31
<212> TYPE: DNA
<213> ORGANISM: Artificial
<220> FEATURE:
<223> OTHER INFORMATION: synthetic construct

<400> SEQUENCE: 72
gcgagggttt agaaaaagat tcaccaaata t         31

<210> SEQ ID NO 73
<211> LENGTH: 18
<212> TYPE: DNA
<213> ORGANISM: Artificial
<220> FEATURE:
<223> OTHER INFORMATION: synthetic construct

<400> SEQUENCE: 73
gggttatcct ccccaata                        18

<210> SEQ ID NO 74
<211> LENGTH: 21
<212> TYPE: DNA
<213> ORGANISM: Artificial
<220> FEATURE:
<223> OTHER INFORMATION: synthetic construct

<400> SEQUENCE: 74
atatgggatg ataaggtgaa a                    21

<210> SEQ ID NO 75
<211> LENGTH: 31
<212> TYPE: DNA
<213> ORGANISM: Artificial
<220> FEATURE:
<223> OTHER INFORMATION: synthetic construct

<400> SEQUENCE: 75
gcgatgcgtt taataagttt tgaaaaatgc c         31

<210> SEQ ID NO 76
<211> LENGTH: 31
<212> TYPE: DNA
<213> ORGANISM: Artificial
<220> FEATURE:
<223> OTHER INFORMATION: synthetic construct

<400> SEQUENCE: 76
gcggaaacca tccttatatg tcaattgctc a         31

<210> SEQ ID NO 77
<211> LENGTH: 24
<212> TYPE: DNA
<213> ORGANISM: Artificial
<220> FEATURE:
<223> OTHER INFORMATION: synthetic construct

<400> SEQUENCE: 77
tttttgttta agttactgta ctgt                 24

<210> SEQ ID NO 78

```
<211> LENGTH: 22
<212> TYPE: DNA
<213> ORGANISM: Artificial
<220> FEATURE:
<223> OTHER INFORMATION: synthetic construct

<400> SEQUENCE: 78
gctagtcttc tacaaccttc ta                                              22

<210> SEQ ID NO 79
<211> LENGTH: 24
<212> TYPE: DNA
<213> ORGANISM: Artificial
<220> FEATURE:
<223> OTHER INFORMATION: synthetic construct

<400> SEQUENCE: 79
gcgtcagggt caagtcatct aaca                                            24

<210> SEQ ID NO 80
<211> LENGTH: 25
<212> TYPE: DNA
<213> ORGANISM: Artificial
<220> FEATURE:
<223> OTHER INFORMATION: synthetic construct

<400> SEQUENCE: 80
gcggacgcat ttcctattga tcaag                                           25

<210> SEQ ID NO 81
<211> LENGTH: 28
<212> TYPE: DNA
<213> ORGANISM: Artificial
<220> FEATURE:
<223> OTHER INFORMATION: synthetic construct

<400> SEQUENCE: 81
gcgagtttcg ccgttaccac ctcagctt                                        28

<210> SEQ ID NO 82
<211> LENGTH: 28
<212> TYPE: DNA
<213> ORGANISM: Artificial
<220> FEATURE:
<223> OTHER INFORMATION: synthetic construct

<400> SEQUENCE: 82
ccctcttatt tcaccctaag acctacaa                                        28

<210> SEQ ID NO 83
<211> LENGTH: 27
<212> TYPE: DNA
<213> ORGANISM: Artificial
<220> FEATURE:
<223> OTHER INFORMATION: synthetic construct

<400> SEQUENCE: 83
gcgacagtcc caataccatt aacaagt                                         27

<210> SEQ ID NO 84
<211> LENGTH: 31
<212> TYPE: DNA
<213> ORGANISM: Artificial
<220> FEATURE:
<223> OTHER INFORMATION: synthetic construct

<400> SEQUENCE: 84
```
gcgtccttag gtacctagaa taattcttca c 31

<210> SEQ ID NO 85
<211> LENGTH: 25
<212> TYPE: DNA
<213> ORGANISM: Artificial
<220> FEATURE:
<223> OTHER INFORMATION: synthetic construct

<400> SEQUENCE: 85
cttttaaatt ataatagcat gatct 25

<210> SEQ ID NO 86
<211> LENGTH: 23
<212> TYPE: DNA
<213> ORGANISM: Artificial
<220> FEATURE:
<223> OTHER INFORMATION: synthetic construct

<400> SEQUENCE: 86
tgctaattta gattacgtta tgt 23

<210> SEQ ID NO 87
<211> LENGTH: 25
<212> TYPE: DNA
<213> ORGANISM: Artificial
<220> FEATURE:
<223> OTHER INFORMATION: synthetic construct

<400> SEQUENCE: 87
catataaaaa tggtcctctc acata 25

<210> SEQ ID NO 88
<211> LENGTH: 23
<212> TYPE: DNA
<213> ORGANISM: Artificial
<220> FEATURE:
<223> OTHER INFORMATION: synthetic construct

<400> SEQUENCE: 88
gcttgagcaa cttacaattc act 23

<210> SEQ ID NO 89
<211> LENGTH: 20
<212> TYPE: DNA
<213> ORGANISM: Artificial
<220> FEATURE:
<223> OTHER INFORMATION: synthetic construct

<400> SEQUENCE: 89
caagctcaag cctcacacat 20

<210> SEQ ID NO 90
<211> LENGTH: 22
<212> TYPE: DNA
<213> ORGANISM: Artificial
<220> FEATURE:
<223> OTHER INFORMATION: synthetic construct

<400> SEQUENCE: 90
tgaccagagt ccaaagttca tc 22

<210> SEQ ID NO 91
<211> LENGTH: 27
<212> TYPE: DNA
<213> ORGANISM: Artificial
<220> FEATURE:

```
<223> OTHER INFORMATION: synthetic construct

<400> SEQUENCE: 91
gcgttaagaa tgcatttatg tttagtc                                        27

<210> SEQ ID NO 92
<211> LENGTH: 25
<212> TYPE: DNA
<213> ORGANISM: Artificial
<220> FEATURE:
<223> OTHER INFORMATION: synthetic construct

<400> SEQUENCE: 92
gcgagttttt ggttggattg agttg                                          25

<210> SEQ ID NO 93
<211> LENGTH: 28
<212> TYPE: DNA
<213> ORGANISM: Artificial
<220> FEATURE:
<223> OTHER INFORMATION: synthetic construct

<400> SEQUENCE: 93
gcgttgttgt ttcaaatgta ttttagtt                                       28

<210> SEQ ID NO 94
<211> LENGTH: 28
<212> TYPE: DNA
<213> ORGANISM: Artificial
<220> FEATURE:
<223> OTHER INFORMATION: synthetic construct

<400> SEQUENCE: 94
gcggacggat catcaaacca atcaagac                                       28

<210> SEQ ID NO 95
<211> LENGTH: 19
<212> TYPE: DNA
<213> ORGANISM: Artificial
<220> FEATURE:
<223> OTHER INFORMATION: synthetic construct

<400> SEQUENCE: 95
ttcaaccatg tcataaaat                                                 19

<210> SEQ ID NO 96
<211> LENGTH: 19
<212> TYPE: DNA
<213> ORGANISM: Artificial
<220> FEATURE:
<223> OTHER INFORMATION: synthetic construct

<400> SEQUENCE: 96
ctcactcctc cataaaaat                                                 19

<210> SEQ ID NO 97
<211> LENGTH: 18
<212> TYPE: DNA
<213> ORGANISM: Artificial
<220> FEATURE:
<223> OTHER INFORMATION: synthetic construct

<400> SEQUENCE: 97
ggaaagaatc agcaaaat                                                  18

<210> SEQ ID NO 98
```

```
<211> LENGTH: 19
<212> TYPE: DNA
<213> ORGANISM: Artificial
<220> FEATURE:
<223> OTHER INFORMATION: synthetic construct

<400> SEQUENCE: 98
cccccacata aataataaa                                               19

<210> SEQ ID NO 99
<211> LENGTH: 26
<212> TYPE: DNA
<213> ORGANISM: Artificial
<220> FEATURE:
<223> OTHER INFORMATION: synthetic construct

<400> SEQUENCE: 99
gcgtgttaat gattgcataa ggttcg                                       26

<210> SEQ ID NO 100
<211> LENGTH: 31
<212> TYPE: DNA
<213> ORGANISM: Artificial
<220> FEATURE:
<223> OTHER INFORMATION: synthetic construct

<400> SEQUENCE: 100
gcgtgtcaaa agaaactcaa taaagaaaaa t                                 31

<210> SEQ ID NO 101
<211> LENGTH: 31
<212> TYPE: DNA
<213> ORGANISM: Artificial
<220> FEATURE:
<223> OTHER INFORMATION: synthetic construct

<400> SEQUENCE: 101
gcgtattccc ttaacaaaat taaagtttca c                                 31

<210> SEQ ID NO 102
<211> LENGTH: 29
<212> TYPE: DNA
<213> ORGANISM: Artificial
<220> FEATURE:
<223> OTHER INFORMATION: synthetic construct

<400> SEQUENCE: 102
gcgcgtcagc ctaacaaaaa gaataaaat                                    29

<210> SEQ ID NO 103
<211> LENGTH: 27
<212> TYPE: DNA
<213> ORGANISM: Artificial
<220> FEATURE:
<223> OTHER INFORMATION: synthetic construct

<400> SEQUENCE: 103
gcggcacgag tcaactttct gtttcct                                      27

<210> SEQ ID NO 104
<211> LENGTH: 24
<212> TYPE: DNA
<213> ORGANISM: Artificial
<220> FEATURE:
<223> OTHER INFORMATION: synthetic construct

<400> SEQUENCE: 104
```

```
gcggaagaag attttcgttt ttat                                          24

<210> SEQ ID NO 105
<211> LENGTH: 20
<212> TYPE: DNA
<213> ORGANISM: Artificial
<220> FEATURE:
<223> OTHER INFORMATION: synthetic construct

<400> SEQUENCE: 105
cgtcgccatc actatgagaa                                               20

<210> SEQ ID NO 106
<211> LENGTH: 24
<212> TYPE: DNA
<213> ORGANISM: Artificial
<220> FEATURE:
<223> OTHER INFORMATION: synthetic construct

<400> SEQUENCE: 106
ccatcttgag cagagtttga agtt                                          24

<210> SEQ ID NO 107
<211> LENGTH: 24
<212> TYPE: DNA
<213> ORGANISM: Artificial
<220> FEATURE:
<223> OTHER INFORMATION: synthetic construct

<400> SEQUENCE: 107
gcgattttgg ttttgtttta ttag                                          24

<210> SEQ ID NO 108
<211> LENGTH: 23
<212> TYPE: DNA
<213> ORGANISM: Artificial
<220> FEATURE:
<223> OTHER INFORMATION: synthetic construct

<400> SEQUENCE: 108
gcggttaaca gccaagttct ttc                                           23

<210> SEQ ID NO 109
<211> LENGTH: 24
<212> TYPE: DNA
<213> ORGANISM: Artificial
<220> FEATURE:
<223> OTHER INFORMATION: synthetic construct

<400> SEQUENCE: 109
gcgatatgct ttgtaagaaa atta                                          24

<210> SEQ ID NO 110
<211> LENGTH: 24
<212> TYPE: DNA
<213> ORGANISM: Artificial
<220> FEATURE:
<223> OTHER INFORMATION: synthetic construct

<400> SEQUENCE: 110
gcgcaagccc aaatattaca aatt                                          24

<210> SEQ ID NO 111
<211> LENGTH: 21
<212> TYPE: DNA
<213> ORGANISM: Artificial
<220> FEATURE:
```

<223> OTHER INFORMATION: synthetic construct

<400> SEQUENCE: 111
gcgcatttgg acttttactt c                                    21

<210> SEQ ID NO 112
<211> LENGTH: 24
<212> TYPE: DNA
<213> ORGANISM: Artificial
<220> FEATURE:
<223> OTHER INFORMATION: synthetic construct

<400> SEQUENCE: 112
gcgacgatgt taattggtag aatc                                 24

<210> SEQ ID NO 113
<211> LENGTH: 25
<212> TYPE: DNA
<213> ORGANISM: Artificial
<220> FEATURE:
<223> OTHER INFORMATION: synthetic construct

<400> SEQUENCE: 113
tcaatcaaca aaacataat tcttc                                 25

<210> SEQ ID NO 114
<211> LENGTH: 25
<212> TYPE: DNA
<213> ORGANISM: Artificial
<220> FEATURE:
<223> OTHER INFORMATION: synthetic construct

<400> SEQUENCE: 114
atttgtgttt tgttttagct ctcta                                25

<210> SEQ ID NO 115
<211> LENGTH: 21
<212> TYPE: DNA
<213> ORGANISM: Artificial
<220> FEATURE:
<223> OTHER INFORMATION: synthetic construct

<400> SEQUENCE: 115
gcgaaactgc ctaggttaaa a                                    21

<210> SEQ ID NO 116
<211> LENGTH: 18
<212> TYPE: DNA
<213> ORGANISM: Artificial
<220> FEATURE:
<223> OTHER INFORMATION: synthetic construct

<400> SEQUENCE: 116
ttaggcgaaa tcaacaat                                        18

<210> SEQ ID NO 117
<211> LENGTH: 20
<212> TYPE: DNA
<213> ORGANISM: Artificial
<220> FEATURE:
<223> OTHER INFORMATION: synthetic construct

<400> SEQUENCE: 117
gcggctggtg attgtgtaat                                      20

<210> SEQ ID NO 118

```
<211> LENGTH: 25
<212> TYPE: DNA
<213> ORGANISM: Artificial
<220> FEATURE:
<223> OTHER INFORMATION: synthetic construct

<400> SEQUENCE: 118
gcgtaatata gttttgtatt gaaat                                      25

<210> SEQ ID NO 119
<211> LENGTH: 16
<212> TYPE: DNA
<213> ORGANISM: Artificial
<220> FEATURE:
<223> OTHER INFORMATION: synthetic construct

<400> SEQUENCE: 119
ctcgctgcta ctggtc                                                16

<210> SEQ ID NO 120
<211> LENGTH: 18
<212> TYPE: DNA
<213> ORGANISM: Artificial
<220> FEATURE:
<223> OTHER INFORMATION: synthetic construct

<400> SEQUENCE: 120
aagaatgcgt tggattta                                              18

<210> SEQ ID NO 121
<211> LENGTH: 28
<212> TYPE: DNA
<213> ORGANISM: Artificial
<220> FEATURE:
<223> OTHER INFORMATION: synthetic construct

<400> SEQUENCE: 121
gcgtactaaa aatggcaatt atttgttg                                   28

<210> SEQ ID NO 122
<211> LENGTH: 28
<212> TYPE: DNA
<213> ORGANISM: Artificial
<220> FEATURE:
<223> OTHER INFORMATION: synthetic construct

<400> SEQUENCE: 122
gcgtgtttca gtatttggat aatagaat                                   28

<210> SEQ ID NO 123
<211> LENGTH: 26
<212> TYPE: DNA
<213> ORGANISM: Artificial
<220> FEATURE:
<223> OTHER INFORMATION: synthetic construct

<400> SEQUENCE: 123
gcgaatatgg cgttgaaaat agtgat                                     26

<210> SEQ ID NO 124
<211> LENGTH: 23
<212> TYPE: DNA
<213> ORGANISM: Artificial
<220> FEATURE:
<223> OTHER INFORMATION: synthetic construct

<400> SEQUENCE: 124
```

```
gcgacccaga ttctgtgcta aga                                           23
```

<210> SEQ ID NO 125
<211> LENGTH: 25
<212> TYPE: DNA
<213> ORGANISM: Artificial
<220> FEATURE:
<223> OTHER INFORMATION: synthetic construct

<400> SEQUENCE: 125

```
gggtgagaaa tacatgcaac ttaca                                         25
```

<210> SEQ ID NO 126
<211> LENGTH: 29
<212> TYPE: DNA
<213> ORGANISM: Artificial
<220> FEATURE:
<223> OTHER INFORMATION: synthetic construct

<400> SEQUENCE: 126

```
gggcatcaaa attgatatta aatgtctaa                                     29
```

<210> SEQ ID NO 127
<211> LENGTH: 20
<212> TYPE: DNA
<213> ORGANISM: Artificial
<220> FEATURE:
<223> OTHER INFORMATION: synthetic construct

<400> SEQUENCE: 127

```
cgcgctagtt gaatgaatgt                                               20
```

<210> SEQ ID NO 128
<211> LENGTH: 21
<212> TYPE: DNA
<213> ORGANISM: Artificial
<220> FEATURE:
<223> OTHER INFORMATION: synthetic construct

<400> SEQUENCE: 128

```
gcgcattgag gaatttttta t                                             21
```

<210> SEQ ID NO 129
<211> LENGTH: 318
<212> TYPE: DNA
<213> ORGANISM: Glycine max

<400> SEQUENCE: 129

```
gatcccctca gcctagcctt cagatgtggc ctgaccagag agcattgaat gaacagcacg    60
ttccttttct tgctccagca ccgtcataca gtggagggat ggttccacct caaggaatgt   120
atccatcttc tgattggagt gggtatcatc aggtaccttt gaatccatat taccctcccg   180
gtgttccttt cccgcatttt ccagctgccc atatgaatca cccgatgtac aaggctgcag   240
atataccagg acatcaacca ccaccatctg atgagtatcc cgagagacct ggccaacctg   300
aatgccagca tttcgtta                                                318
```

<210> SEQ ID NO 130
<211> LENGTH: 138
<212> TYPE: DNA
<213> ORGANISM: Glycine max

<400> SEQUENCE: 130

```
taacgcgaaa gggggaacat cttatatgaa taataataaa tggagaaaag gaaaagaatc    60
```

| | |
|---|---|
| acaggttcca ggttttttcc ttttataccc tccttttctt cctaaattct gaggtttcac | 120 |
| cataaccata ttgggatc | 138 |

<210> SEQ ID NO 131
<211> LENGTH: 1711
<212> TYPE: DNA
<213> ORGANISM: Glycine max

<400> SEQUENCE: 131

| | |
|---|---|
| gaattctgaa attgggtctt tttgtgggca cttttgatg tttttgttta agttactgta | 60 |
| ctgtgggcca caaacgtat agatcaaagt agtaataata atattgatta aatgatatat | 120 |
| atatatatat atatatatat atatctagaa ggttgtagaa gactagctag aacgtacgta | 180 |
| ttcgtgtgga gaagtcctga agtttatcga atcatctaaa actgctaaaa tagcaaacaa | 240 |
| cattatattg taaacaatat ttttctggaa catacaagag tatcctttca cttcctttaa | 300 |
| atacctcgag tgtccccatt gacatcatca aacaagagaa gagttacaga atttcctgtt | 360 |
| tacgatctca ttacaatttt gcaactttca aagcttatta gctaaagtaa catcaaaaga | 420 |
| tgtcattgat tccaagtatt ttcggtggcc aaggagcaa cgtgttcgat ccattctcac | 480 |
| tcgatatgtg ggatcccttc aaggattttc atgttcccac ttcttctgtt tctgctgaaa | 540 |
| attctgcatt tgtgaacaca cgtgtggatt ggaaggagac ccaagaggca cacgtgctca | 600 |
| aggctgatat tccagggctg aagaaagagg aagtgaaggt tcagattgaa gatgataggg | 660 |
| ttcttcagat tagcggagag aggaacgttg agaaggaaga caagaacgac acgtggcatc | 720 |
| gcgtggaccg tagcagtgga aagttcatga aaggttcag attgccagag aatgcaaaag | 780 |
| tggagcaagt aaaggcttgt atggaaaatg gggttctcac tgttactatt ccaaaggaag | 840 |
| aggttaagaa gtctgatgtt aagcctatag aaatctctgg ttaaacttgg tttcactgaa | 900 |
| aatcgtgaga gcttttaaat ttgctttgtt gtaataagtg tcctttgtct tgtgttccaa | 960 |
| tggtgatttt gagaaagatc atacaattgt gccttgtgtt ttgtgcaag tgtaattgaa | 1020 |
| gtgaataaaa aattaacacc tgctttcaga aaattttgct gtgtgtcatt gtcatcgaat | 1080 |
| atgtgatgta ggcaagaaat agaccgtgaa ataatatct gacatttggc taattgcttt | 1140 |
| tgttatgctg agacactcta tgtgaaataa ctgcatttat catgttccat cttcttaata | 1200 |
| caagaagtca ataccaatgt cttaccaaat taagataaca ggtgatttg gactcatcaa | 1260 |
| agtgcagccc tttatttgga ctcatcaaag tgcagcacta aagggttttg ttaactagca | 1320 |
| agttcagagc atcatttaag taattaaaag aaaaaatatt aaatatataa atcataagat | 1380 |
| gatatcaaaa aattcatgaa cagtctcttc atttttttc aataaaaata ttttattt | 1440 |
| aattttttaa aataatatcc tcataacatt ggtttaactc ccaagtttaa aatttactag | 1500 |
| tgctagataa attctctaag ataatgtata gataaaaata agataaatta gaaaattttt | 1560 |
| aaggagagat tttttttat aaaaattagg tatatgtatt ggttttagtt tacagagaaa | 1620 |
| tataatttat atttctttt tgtgtaaata ttaatgaaaa aaattattca aattcaattc | 1680 |
| taaatcttaa tattttttt gacagaattc t | 1711 |

<210> SEQ ID NO 132
<211> LENGTH: 548
<212> TYPE: DNA
<213> ORGANISM: Glycine max

<400> SEQUENCE: 132

| | |
|---|---|
| gccgtcgcct tagccggagc tgcaggctcc gtgccttgct ccgccgccat catcggtgcc | 60 |

-continued

```
tcgctcctgt tgtctctcat gactgcgttt gacgttttaa gattctatat atagtttgca    120
tttcatgaat tattattcca aaataatata tagagagata ataaactgtt agattgcgag    180
tttcgccgtt accacctcag cttattttat gattattatt attattatta ttattattat    240
tattattatt attattatta ttattattat tattaattgt tgtaggtctt agggtgaaat    300
aagagggatt ttgatcctct ctacattttt attgttaatt atgtaatgct atatattatg    360
tatgggtata atttagatcc agtcatttta tgtttctcat gttcttttt ttaatttatc     420 acttctataa agaaaataac ttaaactcaa aatacttata ataacatagc tgatacattt    480
atattatatc cactaaatta tttgatatat gagcagtatc gtagtggtat aggtttgaat    540
gtcagagg                                                              548

<210> SEQ ID NO 133
<211> LENGTH: 345
<212> TYPE: DNA
<213> ORGANISM: Glycine max

<400> SEQUENCE: 133
taaagctgca ccagctagca tttccttgat atcaataccc tgcaatgcag ctggaagtaa     60
acccacagct gacatttctg aagtcctacc accaacccaa tcaaacatag gaaaccgagc    120
taaccatccc tctattctag cagcggtatc caacagagaa ttttcttgag taattgcaac    180
accctgtttt gagaattgca gccctgcatc tctgaaggct ttccgtactt ctagtagacc    240
attgcgggtt tcaggtgtgc ctccgctctt agaaatgaca attacaagag tagttgccag    300
ttcaggtcct agttgagcaa tttgatgatc aatcccagca ggatc                    345

<210> SEQ ID NO 134
<211> LENGTH: 461
<212> TYPE: DNA
<213> ORGANISM: Glycine max

<400> SEQUENCE: 134
aatcattaac atataccatt agaatatgtt aatgattgca taaggttcgg gcacccacta     60
tgcctcttac acatataata tatatatata tatatatata ttttgctgat taaaaaaaaa    120
ctattagaat atgttattct cagtcttagt ttattttaga cttttagatt ttgagtagtt    180
acatattaac attctaaata gtgcaaatac tatattgaaa attcattatt tttctttatt    240
gagtttcttt tgacatatta taattacatt acttagatag actacttata tttctttctg    300
tatatatgat aaggtgtatt actaaccca ctagagctac aactacaact aaagaaataa     360
tataaaacta tgaatatcaa tcttctgtgt tttcatttaa ttatattcgg ttataaaaca    420
ataacagctc ataaaacaat aattattgaa atttaaaatc c                        461
```